United States Patent
Marmorstein et al.

(10) Patent No.: US 9,447,060 B2
(45) Date of Patent: Sep. 20, 2016

(54) SMALL MOLECULE MODULATORS OF PRB INACTIVATION

(71) Applicant: The Wistar Institute of Anatomy and Biology, Philadelphia, PA (US)

(72) Inventors: Ronen Marmorstein, Swarthmore, PA (US); Daniela Fera, Cambridge, MA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 14/356,979

(22) PCT Filed: Nov. 6, 2012

(86) PCT No.: PCT/US2012/063683
§ 371 (c)(1),
(2) Date: May 8, 2014

(87) PCT Pub. No.: WO2013/070586
PCT Pub. Date: May 16, 2013

(65) Prior Publication Data
US 2014/0323442 A1  Oct. 30, 2014

Related U.S. Application Data

(60) Provisional application No. 61/558,686, filed on Nov. 11, 2011.

(51) Int. Cl.
*A61K 31/43* (2006.01)
*C07D 285/08* (2006.01)
(Continued)

(52) U.S. Cl.
CPC ........... *C07D 285/08* (2013.01); *A61K 31/185* (2013.01); *A61K 31/194* (2013.01);
(Continued)

(58) Field of Classification Search
CPC .................................................. A61K 31/433

USPC ........................................................ 514/361
See application file for complete search history.

(56) References Cited

FOREIGN PATENT DOCUMENTS

WO  WO-2006/045581  5/2006

OTHER PUBLICATIONS

Cordon-Cardo, C. et al., Genetic studies and molecular markers of bladder cancer, Seminars in Surgical Oncology, Sep.-Oct. 1997, 13(5): 319-327.

(Continued)

*Primary Examiner* — Shengjun Wang
(74) *Attorney, Agent, or Firm* — Howson & Howson LLP

(57) ABSTRACT

The present invention provides a small molecule treatment of diseases/conditions caused by a virus carrying a viral oncoprotein. In one embodiment, the virus which carries the viral oncoprotein is HPV. The small molecule useful herein includes thiadiazolin-3,5-dione compounds having an optionally substituted aryl group bound to one nitrogen atom of said thiadiazolin-3,5-dione compound. The small molecules may also be administered with a compound which inhibits binding of HPV E6 to p53. In one embodiment, the thiadiazolin-3,5-dione compound has formula (I), or a pharmaceutically acceptable salt, prodrug, solvate, or metabolite thereof, wherein $R^1$ and $R^2$ are defined herein.

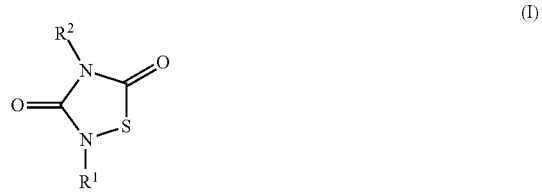

13 Claims, 5 Drawing Sheets

(51) Int. Cl.
 A61K 45/06 (2006.01)
 A61K 31/433 (2006.01)
 A61K 31/185 (2006.01)
 A61K 31/194 (2006.01)
 A61K 31/196 (2006.01)
 A61K 31/351 (2006.01)
 A61K 31/409 (2006.01)
 A61K 31/66 (2006.01)
 A61N 5/10 (2006.01)
(52) U.S. Cl.
 CPC ........... A61K 31/196 (2013.01); A61K 31/351 (2013.01); A61K 31/409 (2013.01); A61K 31/433 (2013.01); A61K 31/66 (2013.01); A61K 45/06 (2013.01); A61N 5/10 (2013.01)

(56) References Cited

OTHER PUBLICATIONS

Devlin, J. et al., High Capacity Screening of Pooled Compounds: Identification of the Active Compound Without Re-Assay of Pool Members, Drug Development Research, Feb. 1996, 37(2): 80-85.
Dufour, X. et al., HPV and head and neck cancer, European Annals of Otorhinolaryngology Head and Neck Diseases, Feb. 2012, 129(1): 26-31.
Ferrand, S. et al., Statistical evaluation of a self-deconvoluting matrix strategy for high-throughput screening of the CXCR3 receptor, Assay Drug Development Technologies, Aug. 2005, 3(4): 413-424.
Harper, D., Currently approved prophylactic HPV vaccines, Expert Review of Vaccines, Dec. 2009, 8(12): 1663-1679.
Kang, N. et al., Identification of small molecules that inhibit GSK-3β through virtual screening, Bioorganic & Medicinal Chemistry Letters, Jan. 15, 2009, 19(2): 533-537.
Lee, J. et al., Structure of the retinoblastoma tumour-suppressor pocket domain bound to a peptide from HPV E7, Feb. 26, 1998, Nature, 391(6670): 859-865.
Liu, X. et al., Structure of the human papillomavirus E7 oncoprotein and its mechanism for inactivation of the retinoblastoma tumor suppressor, Journal of Biological Chemistry, Jan. 6, 2006, 281(1): 578-586.
Martinez, A. et al., TDZD: Selective GSK-3 inhibitors with great potential for Alzheimer disease, Neurobiology of Aging, Apr. 2006, 27: S13.
Martinez, A. et al., SAR and 3D-QSAR studies on thiadiazolidinone derivatives: Exploration of structural requirements for glycogen synthase kinase 3 inhibitors, Journal of Medicinal Chemistry, Nov. 17, 2005, 48(23):7103-7112.
Martinez, A. et al., First non-ATP competitive glycogen synthase kinase 3 β (GSK-3β) inhibitors: Thiadiazolidinones (TDZD) as potential drugs for the treatment of Alzheimer's disease, Journal of Medicinal Chemistry, Mar. 14, 2002, 45(6):1292-1299.
Rosa, A. et al., Antidepressant-like effect of the novel thiadiazolidinone NP031115 in mice, Progress in Neuro-Psychopharmacology & Biological Psychiatry, Aug. 1, 2008; e-publication: Jun. 25, 2008, 32(6):1549-1556.
Rubin, S. et al., Structure of the RbC-terminal domain bound to E2F1-DP1: A mechanism for phosphorylation-induced E2F release, Dec. 16, 2005, Cell, 123(6):1093-1106.
Ruegg, U. et al., Staurosporine, K-252 and UCN-01: potent but nonspecific inhibitors of protein kinases, Trends in Pharmacological Sciences, Jun. 1989, 10(6):218-220.
Schubert, E. et al., The retinoblastoma gene and its dignificance, Annals of Medicine, Jun. 1994, 26(3):177-184.
Stevaux, O. et al., A revised picture of the E2F transcriptional network and RB function, Current Opinion in Cell Biology, Dec. 2002, 14(6):684-691.
Sudhorr, H. et al., Evidence for a causal association for HPV in head and neck cancers, European Archives of Otorhinolaryngology, Nov. 2011; e-publication: Jul. 27, 2011, 268(11):1541-1547.

Adams, Retinoblastoma protein contains a C-terminal motif that targets it for phosphorylation by cyclin-cdk complexes, Molecular and Cellular Biology 19:1068-1080, Feb. 1999.
Baleja, Identification of inhibitors to papillomavirus type 16 E6 protein based on three-dimensional structures of interacting proteins, Antiviral Research, 72(1):49-59, Oct. 1, 2006.
Balog, Crystal structure of the unliganded retinoblastoma protein pocket domain, Proteins, 79:2010-2014, Jun. 2011.
Boyer, E7 protein of human papilloma virus-16 induces degradation of retinoblastoma protein through the ubiquitin-proteasome pathway, Cancer Research, 56: 4620-4624, Oct. 15, 1996.
Burd, Human papillomavirus and cervical cancer, Clinical Microbiology Reviews 16(1): 1-17, Jan. 2003.
Dahiya, Role of the LXCXE binding site in Rb function, Molecular and Cellular Biology 20(18):6799-6805, Sep. 2000.
Defilippis, Endogenous human papillomavirus E6 and E7 proteins differentially regulate proliferation, senescence, and apoptosis in HeLa cervical carcinoma cells, Journal of Virology, 77(2):1551-1563, Jan. 2003.
Felsani, Retinoblastoma family proteins as key targets of the small DNA virus oncoproteins, Oncogene 25(38):5277-5285, Aug. 28, 2006.
Fera, Identification and characterization of small molecule antagonists of pRb inactivation by viral oncoproteins, Chemistry & Biology, 19(4):518-528, Apr. 20, 2012.
Ganguly, Human papillomavirus E6 and E7 oncoproteins as risk factors for tumorigenesis, Journal of Biosciences 34(1):113-123, Mar. 2009.
Gonzalez, Degradation of the retinoblastoma tumor suppressor by the human papillomavirus type 16 E7 oncoprotein is important for functional inactivation and is separable from proteasomal degradation of E7, Journal of Virology 75(16):7583-7591, Aug. 2001.
Harbour, The Rb/E2F pathway: expanding roles and emerging paradigms, Genes & Development, 14(19):2393-2409, Oct. 1, 2000.
Harbour, Cdk phosphorylation triggers sequential intramolecular interactions that progressively block Rb functions as cells move through G1, Cell 98(6):859-869, Sep. 17, 1999.
Hensel, Altered structure and expression of the human retinoblastoma susceptibility gene in small cell lung cancer, Cancer Research, 50(10):3067-3072, May 15, 1990.
Kitchin, Pleiotropic effects of the gene for retinoblastoma, Journal of Medicinal Genetics, 11(3):244-246, Sep. 1974.
Liu, When viral oncoprotein meets tumor suppressor: a structural view, Genes & Development, 20(17):2332-2337, Sep. 1, 2006.
Luna-Medina, Regulation of inflammatory response in neural cells in vitro by thiadiazolidinones derivatives through peroxisome proliferator-activated receptor gamma activation, Journal of Biological Chemistry 280(22):21453-21462, Jun. 3, 2005; e-publication: Apr. 6, 2005.
Luna-Medina, NP031112, a thiadiazolidinone compound, prevents inflammation and neurodegeneration under excitotoxic conditions: Potential therapeutic role in brain disorders, Journal of Neuroscience 27(21):5766-5776, May 23, 2007.
McLaughlin-Drubin, Oncogenic activities of human papillomaviruses, Virus Research, 143(2):195-208, Aug. 2009; e-publication: Jun. 18, 2009.
Motelkar, Evaluation of an orthogonal pooling strategy for rapid high-throughput screening of proteases, Assay and Drug Development Technology, 6(3):395-405, Jun. 2008.
Munger, Biological activities and molecular targets of the human papillomavirus E7 oncoprotein, Oncogene 20(54):7888-7898, Nov. 26, 2001.
Scheffner, The state of the p53 and retinoblastoma genes in human cervical carcinoma cell lines, Proceedings National Academy of Sciences, USA, 88(13):5523-5527, Jul. 1, 1991.
Singh, Molecular determinants for the complex formation between the retinoblastoma protein and LXCXE sequences, Journal of Biological Chemistry 280(45):37868-37876, Nov. 11, 2005; e-publication: Aug. 23, 2005.
Xiao, Crystal structure of the retinoblastoma tumor suppressor protein bound to E2F and the molecular basis of its regulation, Proceedings of the National Academy of Sciences, USA, 100(5):2363-2368, Mar. 4, 2003; e-publication: Feb. 21, 2003.

(56) References Cited

OTHER PUBLICATIONS

Yee, Presence and expression of human papillomavirus sequences in human cervical carcinoma cell lines, American Journal of Pathology, 119(3):361-366, Jun. 1985.

Zhang, A Simple Statistical Parameter for Use in Evaluation and Validation of High Throughput Screening Assays, Journal of Biomolecular Screening, 4(2):67-73, Apr. 1999.

International Search Report dated Feb. 1, 2013 and issued in International Patent Application No. PCT/US0212/063683.

Malik, S et al., Thiazolidinediones: A Plethro of Biological Load, Internatl J PharmTech Res., 3,(1):62-75 (Jan.-Mar. 2011).

Nawale, SL and Dhake, AS, Synthesis and evaluation of novel thiazolidinedione derivatives for antibacterial activity, Der Pharma Chemica, 2012, 4(6):2270-2277.

D'Abramo, CM et al, Small Molecule Inhibitors of Human Papillomavirus Protein-Protein Interactions, The Open Virology J., 5:80-95 (published on-line Jul. 2011).

A.

B.

A.

B.

SEQUENCE LISTING

```
<160> NUMBER OF SEQ ID NOS: 5

<210> SEQ ID NO 1
<211> LENGTH: 98
<212> TYPE: PRT
<213> ORGANISM: Unknown
<220> FEATURE:
<223> OTHER INFORMATION: HPV16-E7

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
```

```
                35                  40                  45
Arg Ala His Tyr Asn Ile Val Thr Phe Cys Cys Lys Cys Asp Ser Thr
 50                  55                  60
Leu Arg Leu Cys Val Gln Ser Thr His Val Asp Ile Arg Thr Leu Glu
65                  70                  75                  80
Asp Leu Leu Met Gly Thr Leu Gly Ile Val Cys Pro Ile Cys Ser Gln
                85                  90                  95
Lys Pro

<210> SEQ ID NO 2
<211> LENGTH: 289
<212> TYPE: PRT
<213> ORGANISM: Unknown
<220> FEATURE:
<223> OTHER INFORMATION: Ad5-E1A

<400> SEQUENCE: 2

Met Arg His Ile Ile Cys His Gly Gly Val Ile Thr Glu Glu Met Ala
1               5                   10                  15
Ala Ser Leu Leu Asp Gln Leu Ile Glu Glu Val Leu Ala Asp Asn Leu
                20                  25                  30
Pro Pro Pro Ser His Phe Glu Pro Thr Leu His Glu Leu Tyr Asp
            35                  40                  45
Leu Asp Val Thr Ala Pro Glu Asp Pro Asn Glu Glu Ala Val Ser Gln
 50                  55                  60
Ile Phe Pro Asp Ser Val Met Leu Ala Val Gln Glu Gly Ile Asp Leu
65                  70                  75                  80
Leu Thr Phe Pro Pro Ala Pro Gly Ser Pro Glu Pro His Leu Ser
                85                  90                  95
Arg Gln Pro Glu Gln Pro Glu Gln Arg Ala Leu Gly Pro Val Ser Met
                100                 105                 110
Pro Asn Leu Val Pro Glu Val Ile Asp Leu Thr Cys His Glu Ala Gly
            115                 120                 125
Phe Pro Pro Ser Asp Asp Glu Asp Glu Glu Gly Glu Glu Phe Val Leu
        130                 135                 140
Asp Tyr Val Glu His Pro Gly His Gly Cys Arg Ser Cys His Tyr His
145                 150                 155                 160
Arg Arg Asn Thr Gly Asp Pro Asp Ile Met Cys Ser Leu Cys Tyr Met
                165                 170                 175
Arg Thr Cys Gly Met Phe Val Tyr Ser Pro Val Ser Glu Pro Glu Pro
                180                 185                 190
Glu Pro Glu Pro Glu Pro Glu Pro Ala Arg Pro Thr Arg Arg Pro Lys
            195                 200                 205
Met Ala Pro Ala Ile Leu Arg Arg Pro Thr Ser Pro Val Ser Arg Glu
        210                 215                 220
Cys Asn Ser Ser Thr Asp Ser Cys Asp Ser Gly Pro Ser Asn Thr Pro
225                 230                 235                 240
Pro Glu Ile His Pro Val Val Pro Leu Cys Pro Ile Lys Pro Val Ala
                245                 250                 255
Val Arg Val Gly Gly Arg Arg Gln Ala Val Glu Cys Ile Glu Asp Leu
                260                 265                 270
Leu Asn Glu Pro Gly Gln Pro Leu Asp Leu Ser Cys Lys Arg Pro Arg
            275                 280                 285
Pro
```

<210> SEQ ID NO 3
<211> LENGTH: 928
<212> TYPE: PRT
<213> ORGANISM: Homo sapiens

<400> SEQUENCE: 3

Met Pro Pro Lys Thr Pro Arg Lys Thr Ala Thr Ala Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
    275                 280                 285

Lys Asn Val Tyr Phe Lys Asn Phe Ile Pro Phe Met Asn Ser Leu Gly
290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Pro Pro His Thr Pro Val Arg Thr Val Met Asn Thr Ile Gln Gln
    370                 375                 380

```
Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
            405                 410                 415

Lys Arg Val Lys Asp Ile Gly Tyr Ile Phe Lys Glu Lys Phe Ala Lys
        420                 425                 430

Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
        450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
            485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Gly Asn Leu Thr Arg
        530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
            565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
        610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
            645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
        690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
            725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
        770                 775                 780

Ile Pro Arg Ser Pro Tyr Lys Phe Pro Ser Ser Pro Leu Arg Ile Pro
785                 790                 795                 800
```

```
Gly Gly Asn Ile Tyr Ile Ser Pro Leu Lys Ser Pro Tyr Lys Ile Ser
            805                 810                 815

Glu Gly Leu Pro Thr Pro Thr Lys Met Thr Pro Arg Ser Arg Ile Leu
        820                 825                 830

Val Ser Ile Gly Glu Ser Phe Gly Thr Ser Glu Lys Phe Gln Lys Ile
    835                 840                 845

Asn Gln Met Val Cys Asn Ser Asp Arg Val Leu Lys Arg Ser Ala Glu
850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925

<210> SEQ ID NO 4
<211> LENGTH: 93
<212> TYPE: PRT
<213> ORGANISM: Unknown
<220> FEATURE:
<223> OTHER INFORMATION: HPV1A-E7

<400> SEQUENCE: 4

Met Val Gly Glu Met Pro Ala Leu Lys Asp Leu Val Leu Gln Leu Glu
1               5                   10                  15

Pro Ser Val Leu Asp Leu Asp Leu Tyr Cys Tyr Glu Glu Val Pro Pro
            20                  25                  30

Asp Asp Ile Glu Glu Glu Leu Val Ser Pro Gln Gln Pro Tyr Ala Val
        35                  40                  45

Val Ala Ser Cys Ala Tyr Cys Glu Lys Leu Val Arg Leu Thr Val Leu
    50                  55                  60

Ala Asp His Ser Ala Ile Arg Gln Leu Glu Glu Leu Leu Leu Arg Ser
65                  70                  75                  80

Leu Asn Ile Val Cys Pro Leu Cys Thr Leu Gln Arg Gln
                85                  90

<210> SEQ ID NO 5
<211> LENGTH: 437
<212> TYPE: PRT
<213> ORGANISM: Homo sapiens

<400> SEQUENCE: 5

Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
        35                  40                  45

Thr Gly Pro Ala Ala Pro Ala Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
```

```
                    100                 105                 110
Arg His Pro Gly Lys Gly Val Lys Ser Pro Gly Glu Lys Ser Arg Tyr
            115                 120                 125

Glu Thr Ser Leu Asn Leu Thr Thr Lys Arg Phe Leu Glu Leu Leu Ser
            130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
            165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
            195                 200                 205

Asp Leu Arg Gln Leu Gln Glu Ser Glu Gln Gln Leu Asp His Leu Met
            210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
            260                 265                 270

Leu Gln Ala Val Asp Ser Ser Glu Asn Phe Gln Ile Ser Leu Lys Ser
            275                 280                 285

Lys Gln Gly Pro Ile Asp Val Phe Leu Cys Pro Glu Glu Thr Val Gly
            290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Pro Ser
                325                 330                 335

Ser Pro Pro Ser Ser Leu Thr Thr Asp Pro Ser Gln Ser Leu Leu Ser
                340                 345                 350

Leu Glu Gln Glu Pro Leu Leu Ser Arg Met Gly Ser Leu Arg Ala Pro
            355                 360                 365

Val Asp Glu Asp Arg Leu Ser Pro Leu Val Ala Ala Asp Ser Leu Leu
            370                 375                 380

Glu His Val Arg Glu Asp Phe Ser Gly Leu Leu Pro Glu Glu Phe Ile
385                 390                 395                 400

Ser Leu Ser Pro Pro His Glu Ala Leu Asp Tyr His Phe Gly Leu Glu
                405                 410                 415

Glu Gly Glu Gly Ile Arg Asp Leu Phe Asp Cys Asp Phe Gly Asp Leu
            420                 425                 430

Thr Pro Leu Asp Phe
            435
```

SMALL MOLECULE MODULATORS OF PRB INACTIVATION

All publications and priority applications, including U.S. Provisional Patent Application No. 61/558,686, filed Nov. 11, 2011, and International Patent Application No. PCT/US2012/63683, filed Nov. 6, 2012, cited in this specification are incorporated herein by reference. While the invention has been described with reference to particular embodiments, it will be appreciated that modifications can be made without departing from the spirit of the invention. Such modifications are intended to fall within the scope of the appended claims.

STATEMENT REGARDING FEDERALLY SPONSORED RESEARCH OR DEVELOPMENT

This invention was made with government support under grant Nos. CA094165, and GM071339 and awarded by the National Institutes of Health. The government has certain rights in the invention.

BACKGROUND

HPV has received considerable attention due to its role in human cancer. In particular, HPV is known to be the causative agent of a number of epithelial cancers, most notably cervical cancer, a leading cause of death for women worldwide. HPV is associated with more than 95% of all cervical cancers, the leading cause of cancer deaths of woman in developing countries due to high HPV infection rates and lack of comprehensive cervical Pap smear testing of susceptible women.

HPV infection has also been implicated to have a causative role in about 20% of head and neck cancers, the majority of anal and vaginal cancers, and about 50% and 35% of vulvar and penile cancers, respectively. There are over 200 HPV genotypes known, and they fall under two general forms: low-risk and high-risk, which cause benign and malignant lesions, respectively. Two prophylactic vaccines are currently available, Gardasil™ and Cervarix® vaccines, which help prevent against infection by the low risk HPV types 6 and 11 and high risk HPV types 16 and 18. While these vaccines target HPV types that cause more than 90% of genital warts and cervical cancer, they have no therapeutic utility, i.e., they cannot treat existing infection. Furthermore, the effectiveness and longevity of these vaccines will not be known for decades, further warranting a need for therapeutics.

What is needed in the art are treatment options for patients infected with oncoviruses, such as HPV.

SUMMARY OF THE INVENTION

In one aspect, composition (A) for treating a HPV mediated disease is provided and contains a (i) a thiadiazolin-3,5-dione compound which has an optionally substituted aryl group bound to one nitrogen atom of said thiadiazolin-3,5-dione compound; and (ii) a compound which inhibits binding of HPV E6 to p53. In one embodiment, the thiadiazolin-3,5-dione compound has formula (I), or a pharmaceutically acceptable salt, prodrug, solvate, or metabolite thereof, wherein $R^1$ and $R^2$ are defined herein.

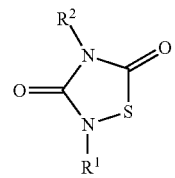

(I)

In another aspect, methods for preventing disruption of pRb/E2F complexes are provided and include administering, to a patient in need thereof, a compound of formula (I) or composition (A).

In a further aspect, methods for preventing interaction between pRb and a viral oncoprotein are provided and include administering, to a patient in need thereof, a compound of formula (I) or composition (A).

In yet another aspect, methods for preventing or a disease caused by a virus carrying a viral oncoprotein containing a L×C×E motif are provided and include administering, to a patient in need thereof, a compound of formula (I) or composition (A).

In still a further aspect, methods for preventing or treating neoplastic disease are provided and include administering, to a patient in need thereof, a compound of formula (I) or composition (A).

In another aspect, a method for preventing HPV-E7 mediated E2F displacement from pRb is provided and includes administering a compound of formula (I) or composition (A) to a patient in need thereof.

In yet another aspect, a method for disrupting pRb/HPV-E7 complexes is provided and includes administering a compound of formula (I) or composition (A) to a patient in need thereof.

In still a further aspect, a method for preventing or treating genital warts is provided and includes administering a compound of formula (I) or composition (A) to a patient in need thereof.

In another aspect, a method for preventing or treating neoplastic disease caused by HPV, adenovirus, or SV40 is provided and includes administering a compound of formula (I) or a composition (A) to a patient in need thereof.

Other aspects and advantages of the invention will be readily apparent from the following detailed description of the invention.

DESCRIPTION OF THE FIGURES

FIG. 2A includes $IC_{50}$ curves for compounds 1-7 and is a plot of concentration (log [compound] (μM)) vs. percentage (%) of E2F remaining bound to pRb. $IC_{50}$ curves were generated using the ELISA-based assay described in Example 2 and correspond to the following:

Figure 1:
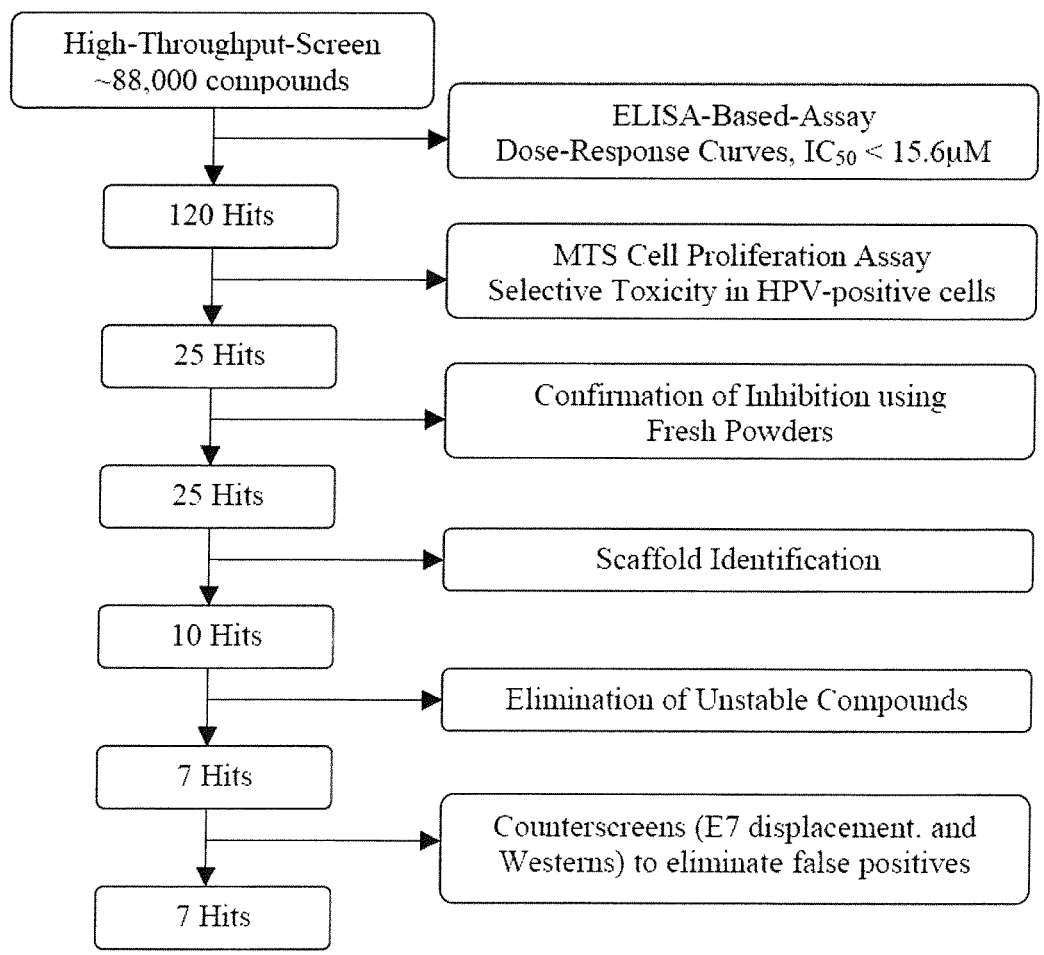
FIG. 1 provides a flowchart summary of the process for the identification of compounds 1-7.

circles (●): compound 2
dark, small squares (■): compound 3
small triangles (▲): compound 6
inverted triangles (▼): compound 1 diamonds (♦): compound 4
light, large squares (■): compound 5
large, triangles (▲): compound 7

Figure 2:
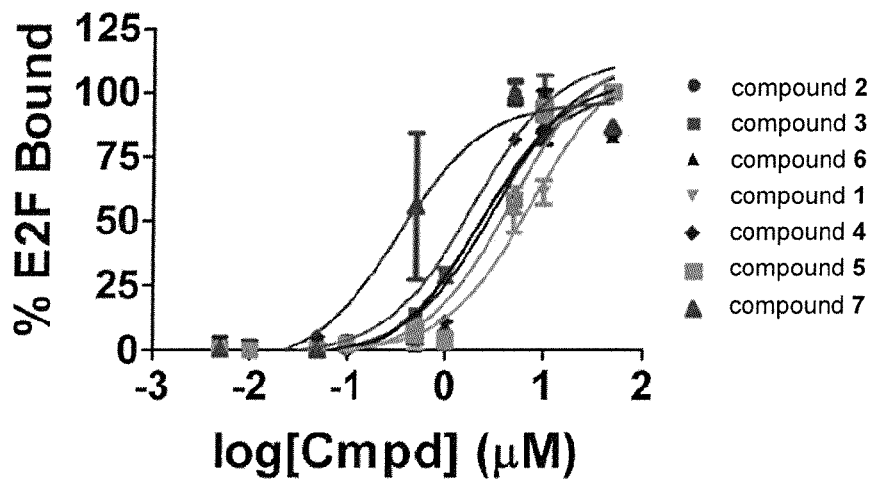
FIG. 2 provides data for thiadiazolin-3,5-dione compounds 1-7. GraphPad® software (Prism) was used for $IC_{50}$ determination and their corresponding errors. To calculate the $IC_{50}$ values, three independent dose-response curves were fit to one-site (Hill slope=1) sigmoidal-dose-response curves. The error bars were obtained from the standard errors generated by GraphPad® software.
Figure 2:
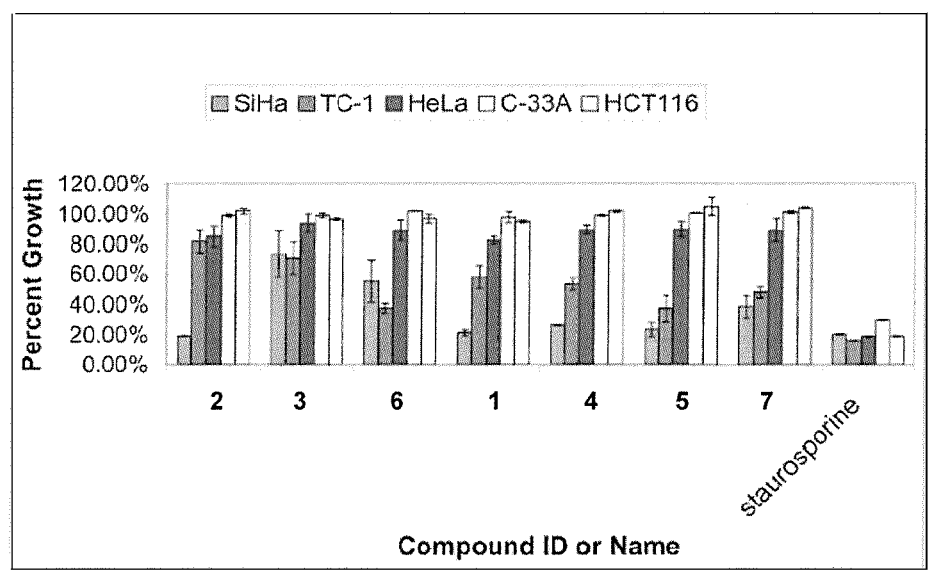

FIG. 2B illustrates the cellular toxicity for compounds 1-7, as discussed in Example 2 (iv), with the results represented by a bar graph. The graph provides the percent growth of four different cervical cancer cells lines, i.e., SiHa, TC-1, HeLa and C-33A and one non-cervical cancer cell line, HCT116, in the presence of compounds 1-7 and staurosporine, which is a positive control due to its expected toxicity in all cells. In each compound result group, the vertical bar on the farthest left represents the percentage growth of the SiHa cells, the second left-most vertical bar for each compound represents the percentage growth of the TC-1 cells, the middle vertical bar for each compound represents the percentage growth of the HeLa cells, the fourth left-most vertical bar for each compound represents the percentage growth of the C-33A cells, and the fifth left-most vertical bar for each compound represents the percentage growth of the HCT116 cells.

Figure 3:
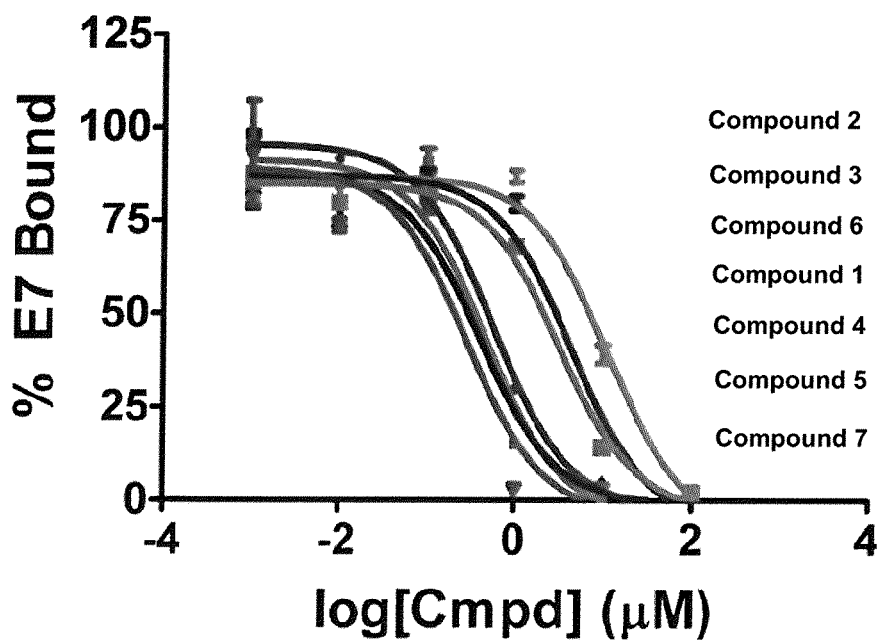
Figure 3:
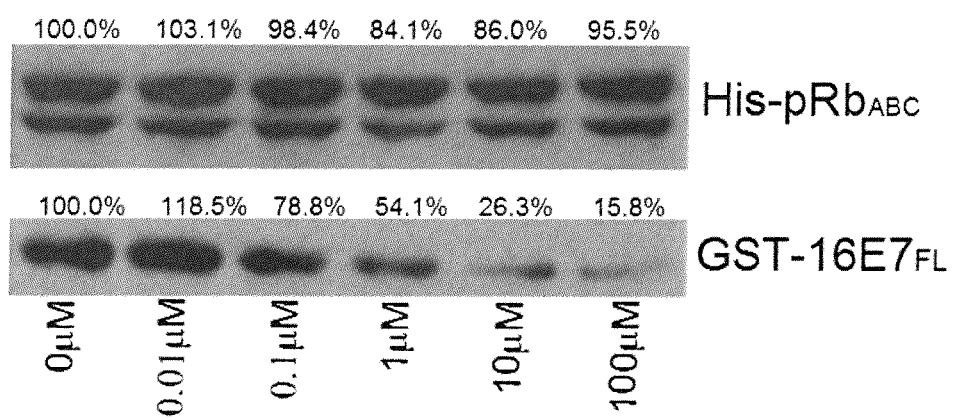

FIG. 3 provides data illustrating disruption of HPV-E7/pRb complexes using compounds 1-7. GraphPad® software (Prism) was used for $IC_{50}$ determination and their corresponding errors. To calculate the $IC_{50}$ values, two independent dose-response curves were fit to one-site (Hill slope=1) sigmoidal-dose-response curves. The error bars were obtained from the standard errors generated by GraphPad® software. FIG. 3A includes $IC_{50}$ curves for compounds 1-7 and the ability of compounds 1-7 to disrupt HPV-E7/pRb complexes. $IC_{50}$ curves were generated using the ELISA-based assay described in Example 2 and correspond to the following:

circles (●): compound 2
dark, small squares (■): compound 3
small triangles (▲): compound 6
inverted triangles (▼): compound 1
diamonds (♦): compound 4
light, large squares (■): compound 5
large, triangles (▲): compound 7

FIG. 3B is a western blot and illustrates the effect of compound 2 on HPV-E7/pRb pull-down. Concentrations of compound 2 (0, 0.01, 0.1, 1, 10, and 100 μM) were independently added and the amount of GST-E7$_{FL}$ remaining bound to pRb was probed by using an anti-GST antibody (bottom panel). The top panel shows the loading control of His-pRb$_{ABC}$ in each lane. The values above each panel provide the quantitative percentage of pRb and GST-16E7$_{FL}$ protein detected following pull-down at each inhibitor concentration.

Figure 4:
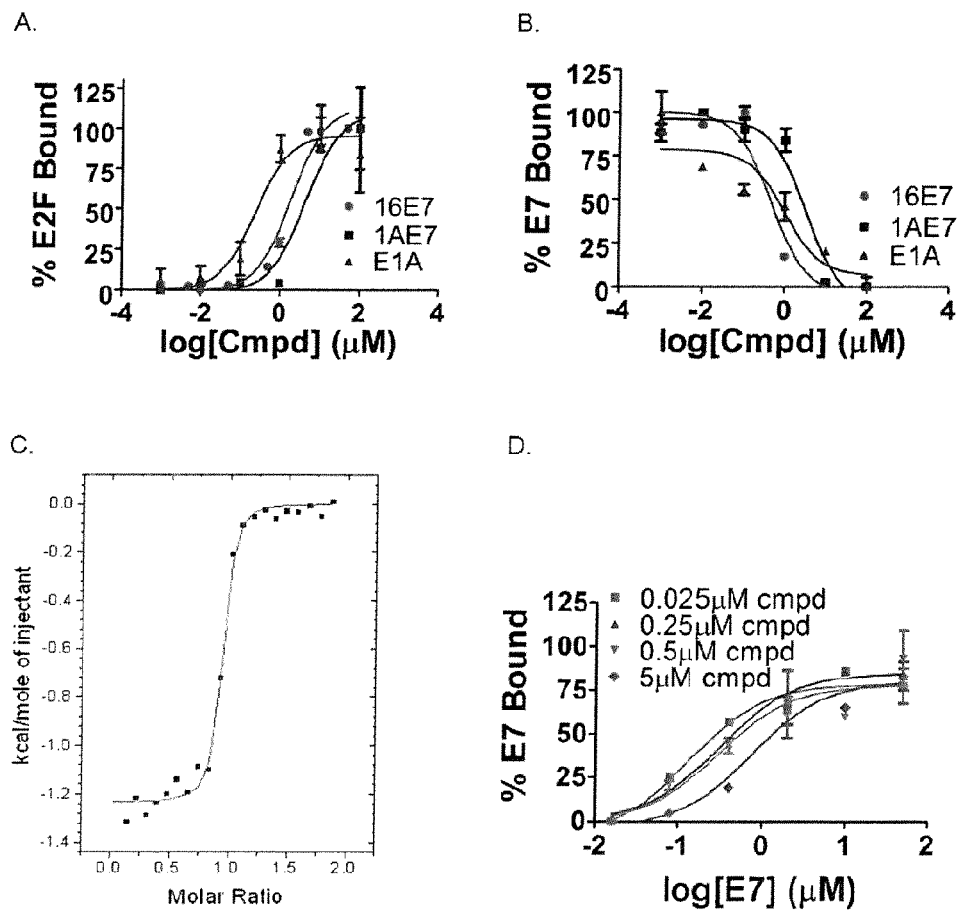

FIG. 4 illustrates the effect of thiadiazolin-3,5-dione compound 2 against viral oncoproteins E7 from high HPV (type 16), 1AE7 from low risk HPV (type 1A), and E1a from adenovirus. GraphPad® software (Prism) was used for $IC_{50}$ determination and their corresponding errors. To calculate the $IC_{50}$ values, three independent dose-response curves were fit to one-site (Hill slope=1) sigmoidal-dose-response curves. The error bars were obtained from the standard errors generated by GraphPad® software. FIG. 4A is a plot of % E2F vs. concentration (log [compound] μM) and illustrates E2F disruption E2F/pRb complexes by LxCxE containing viral oncoproteins 16E7 (circles (●)), 1AE7 (squares ■)), or E1A (triangles (▲)) in the presence of compound 2 by adding ten-fold dilutions of compound 2 to GST-pRb$_{ABC}$/6xHis-HPV1AE7$_{CR2-3}$ or GST-pRb$_{ABC}$/6xHis-Ad5E1A$_{CR2-3}$. FIG. 4B is a plot of % E7 vs. (log [compound] μM) and illustrates the disruption of complexes between pRb and LxCxE containing viral oncoproteins 16E7 (circles (●)), 1AE7 (squares ■)), or E1A (triangles (▲)) in the presence of compound 2. FIG. 4C shows the binding of thiadiazolin-3,5-dione compound 2 to pRb as a plot of the molar ratio of compound 2 vs. integrated heats (kcal/mole) of compound 2 as measured by isothermal titration calorimetry. Integrated heats show the binding of compound 2 directly to pRb. The curve fit to a 1:1 binding model, with a $K_D$ of 165 nM. FIG. 4D shows the ability of HPV-E7 to disrupt complexes of pRb and compound 2 using increasing concentrations (0.025, 0.25, 0.5, and 5 μM) of compound 2. The plot is a measure of concentration (log [E7] (μM)) vs. % E7. Five-fold dilutions of E7 were added to pRb/compound 2 complexes and the amount of E7 that was able to bind to pRb was determined.

Figure 5:
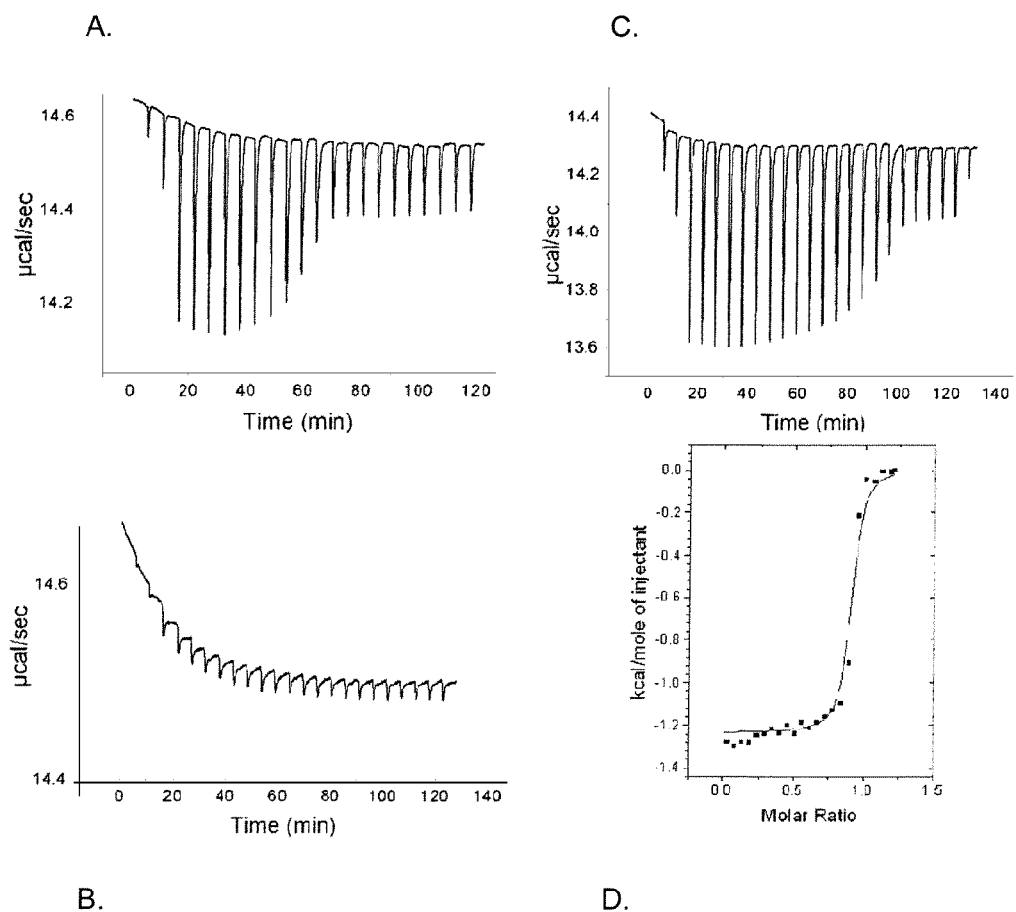

FIG. 5 illustrates the reversibility of compound 3 in binding to pRb as measured by isothermal titration calorimetry. FIGS. 5A-5B show the incremental heat effects of 10 μL titrations of 750 μM of compound 3 into pRb and buffer, respectively, and plot the heat generated (pcal/sec) vs. time (min) FIG. 5C shows the incremental heat effects of 8 μL titrations of compound 3 into pRb solutions after pRb/compound complexes were dialyzed overnight to remove the unbound compound and is a plot of the heat generated (μcal/sec) vs. time (min). This binding curve provides a dissociation constant and stoichiometry, indicating that compound 3 interacted with pRb in a reversible fashion. FIG. 5D represents the binding curves for 6xHis-HPV16-E7$_{CR2-3}$ mediated displacement of E2F$_{MB-TA}$ from GST-pRb$_{ABC}$ in the presence of varying concentrations of inhibitor, above and below the dissociation constant of pRb for inhibitor. This data shows a dependence on the concentration of inhibitor used, where increasing inhibitor concentration is correlated with a rightward shift (higher apparent value) in the $IC_{50}$ values for HPV-E7 mediated displacement of pRb/E2F complex. This data suggests that inhibitor and HPV16-E7 bind competitively to pRb. Taking this result together with the observation that these inhibitors are also able to disrupt pRb complexes with HPV1A-E7 and AD5-E1a (FIG. 5A) suggests that these inhibitors also bind pRb competitively with other LxCxE containing oncoproteins.

DETAILED DESCRIPTION OF THE INVENTION

In recognizing the need in the art for therapies for treating diseases caused by certain oncoviruses, the inventors identified a family of small molecules based on a thiadiazolin-3,5-dione backbone. These thiadiazolin-3,5-dione compounds unexpectedly inhibited the ability of viral oncoproteins to disrupt pRb/E2F complexes by undesirably displacing E2F and thereby inactivating the function of the pRb transcription factor. This finding is integral in the treatment of certain cancers where there are no known small molecule drug therapies.

As used herein, retinoblastoma transcription factor (referred to as "pRb" herein) is a protein that regulates cell cycle, apoptosis and differentiation through its direct binding to and inhibition of the E2F family of transcription factors. pRb becomes phosphorylated by cyclin/cyclin dependent kinases (cdks), which then signals pRb to release E2F proteins to transcribe genes necessary for the progression into the S-phase of the cell cycle, as well as for DNA replication. The A and B cyclin fold domains of pRb form a "pocket" region of the protein, which forms a groove that makes high affinity contacts to the transactivation domain of E2F. While the A/B pocket of pRb is important for its biological activity, the C-terminal domain is important for the formation of physiological pRb-E2F complexes. The C-terminal domain of pRb makes contact with the marked-box region of E2F, although with a lower affinity. This domain of pRb is also subject to cell-cycle dependent posttranslational modifications, such as phosphorylation and acetylation, as well as the recruitment of cyclins/cdks.

pRb is also a target for inactivation by viral oncoproteins, including those specified below. Viral oncoproteins bind to hypophosphorylated pRb, disrupting pRb/E2F complexes and thereby leading to dysregulated entry into S-phase of the cell cycle and neoplasia. Each viral oncoprotein that inhibits pRb function employs a conserved LxCxE for high affinity pRb binding. The LxCxE motif from viral oncoproteins contributes to disruption of the pRb/E2F complexes by binding to the pRb B domain. The C-terminal domain of pRb is the target of other regions of the viral oncoproteins. Each oncoprotein uses different protein regions to displace pRb/E2F complexes through distinct mechanisms.

The inventors found that thiadiazolin-3,5-dione compounds bind directly and competitively to the LxCxE binding site of pRb with dissociation constants in the mid-high nanomolar range. The thiadiazolin-3,5-dione compounds are also competitive for pRb binding to other viral oncoproteins containing an LxCxE motif. Therefore, in one embodiment, these thiadiazolin-3,5-dione are inhibitors. In yet another embodiment, the thiadiazolin-3,5-dione compounds prevent disruption of pRb/E2F complexes. In a further embodiment, the thiadiazolin-3,5-dione compounds prevent interactions between pRb and a viral oncoprotein.

These thiadiazolin-3,5-dione compounds are the first class of small molecules that competitively inhibit the interaction of LxCxE motif-containing viral oncoproteins with pRb. The identification of these thiadiazolin-3,5-dione compounds is an important finding given that there are no known inhibitors that specifically block the interaction of pRb with viral oncoproteins. In one embodiment, the thiadiazolin-3,5-dione compounds bind to pRb. In another embodiment, the thiadiazolin-3,5-dione compounds bind to the LxCxE binding site of pRb. In a further embodiment, the thiadiazolin-3,5-dione compounds prevent one of the main transforming abilities of these oncoproteins, i.e., the premature disruption of the inhibitory pRb/E2F complex. In still another embodiment, the thiadiazolin-3,5-dione compounds reduce or prevent pRb degradation in HPV containing cells.

Of significance, the inventors found that these thiadiazolin-3,5-dione compounds are highly selective. In one embodiment, the thiadiazolin-3,5-dione compounds exhibit selective cytotoxicity in HPV positive cells.

The terms "patient" and "subject" are used interchangeably and refer to a mammal, preferably a human, who is infected with an oncogenic virus that disrupts or inactivates normal pRb binding, such as HPV. The patient may be an adult or child. A "patient" or "subject" may also include a veterinary or farm animal, a domestic animal or pet, and animals normally used for clinical research. In one embodiment, the patient or subject is a human.

The terms "oncogenic virus" and "oncovirus", which are used interchangeably, describe viruses that cause cancer. In one embodiment, the oncovirus causes or mediates malignant transformation of cells, inducing a neoplasia in a patient. In one embodiment, the oncovirus is a papovavirus such as human papilloma virus (HPV). In another embodiment, the oncovirus is a Herpes virus such as Kaposi's sarcoma-associated herpes virus (KSHV or HHV-8) or Epstein-Barr virus (EBV). In a further embodiment, the oncovirus is a hepatitis virus, such as Hepatitis B virus (HBV) and Hepatitis C virus (HCV). In yet another embodiment, the oncogenic virus is an Adenovirus. In still a further embodiment, the oncovirus is a Poxvirus. In another embodiment, the oncovirus is a Retrovirus. In yet a further embodiment, the oncovirus is a Human T-cell Leukemia Virus. In another embodiment, the oncovirus is a polyoma virus such as Merkel cell polyoma virus. In another embodiment, the oncovirus is simian virus 40 (SV40).

The term "viral oncoprotein" describes a viral protein that is involved in the regulation or synthesis of proteins linked to tumorigenic cell growth. In a further embodiment, the viral oncoprotein targets, disrupts or inactivates pRb. In a further embodiment, the viral oncoprotein contains a LxCxE motif. In a further embodiment, the viral oncoprotein is E1a from adenovirus. In a further embodiment, the viral oncoprotein is E7 from high HPV. In a further embodiment, the viral oncoprotein is 1AE7 from low risk HPV. In another embodiment, the viral oncoprotein is T-antigen from simian virus 40 (SV40).

The thiadiazolin-3,5-dione compounds, therefore, are useful in the treatment or prevention of a variety of conditions/diseases. In one embodiment, the thiadiazolin-3,5-dione compounds are useful in methods for preventing or treating a disease caused by an oncovirus containing an oncoprotein that targets, disrupts or inactivates pRb. In another embodiment, the thiadiazolin-3,5-dione compounds are useful in methods for preventing or treating neoplastic disease. In a further embodiment, the compounds are useful in methods for prevention or treating HPV infection. In a further embodiment, the thiadiazolin-3,5-dione compounds are useful in methods for preventing or treating HPV-E7 mediated E2F displacement from pRb. In still another embodiment, the thiadiazolin-3,5-dione compounds are useful in methods for disrupting pRb/HPV-E7 complexes. In another embodiment, the thiadiazolin-3,5-dione compounds are useful in methods for preventing or treating benign conditions caused by oncovirus containing an oncoprotein that targets, disrupts or inactivates pRb. In yet a further embodiment, the thiadiazolin-3,5-dione compounds are useful in methods for preventing or treating genital warts. In another embodiment, the thiadiazolin-3,5-dione compounds are useful in methods for preventing or treating neoplastic disease caused by human papilloma virus.

The term "neoplastic disease" as used herein refers to a disease or condition in which a patient has an abnormal mass of tissue due to an abnormal proliferation of cells. The abnormal proliferation of cells may result in a localized lump, be present in the lymphatic system, or may be systemic. In another embodiment, the neoplastic disease is caused by HPV infection, both low and high risk forms. In one embodiment, the neoplastic disease is benign. In another embodiment, the neoplastic disease is pre-malignant, i.e., potentially malignant neoplastic disease. In a further embodiment, the neoplastic disease is malignant, i.e., cancer.

The neoplastic diseases (cancers) caused by these oncoviruses are numerous, but may be treated using the compounds, compositions and methods described herein. In one embodiment, the neoplastic disease is an epithelial cancer, both low and high risk cancers. In another embodiment, the neoplastic disease is Kaposi's sarcoma (a skin cancer associated with KSHV or HHV-8), Merkel cell carcinoma, hepatocellular carcinoma (liver cancer), cervical cancer, anal cancer, penile cancer, vulvar cancer, vaginal cancer, neck cancer, head cancer, Kaposi's sarcoma, multicentric Castleman's disease, primary effusion lymphoma, tropical spastic paraparesis, adult T-cell leukemia, Burkitt's lymphoma, Hodgkin's lymphoma, post-transplantation lymphoproliferative disease, nasopharyngeal carcinoma, pleural mesothelioma cancer of the lining of the lung), osteosarcoma (a bone cancer), ependymoma and choroid plexus tumors of the brain, and non-Hodgkin's lymphoma. In another embodiment, the neoplastic disease is caused by HPV infection, both low and high risk forms. In a further embodiment, the neoplastic disease is cervical cancer. In a further embodiment, the neoplastic disease is anal cancer. In still a further embodiment, the neoplastic disease is penile cancer. In another embodiment, the neoplastic disease is vulvar cancer. In yet a further embodiment, the neoplastic disease is vaginal cancer. In another embodiment, the neoplastic disease is neck cancer. In still a further embodiment, the neoplastic disease is head cancer such as eye cancer. Still other diseases caused by one of the exemplary pRb inactivating oncovirues are anticipated to be included with classical neoplastic diseases as suitable for treatment with the compounds and methods disclosed herein.

The term "benign" condition as used herein refers to a condition which is not a neoplastic disease, i.e., the benign condition is not cancer. The benign condition is caused by an oncovirus containing an oncoprotein that targets, disrupts or inactivates pRb, such as HPV. In one embodiment, the benign condition is warts. In another embodiment, the benign condition is skin warts such as common warts, plantar warts, subungal warts, or periungual warts, or flat warts. In a further embodiment, the benign condition is genital warts. In still another embodiment, the benign condition is anal warts. In yet a further embodiment, the benign condition is respiratory papillomatosis. In another embodiment, the benign condition is epidermodysplasia verruciformis I. The Thiadiazolidinedione Compounds As discussed above, the inventors found thiadiazolin-3,5-dione compounds which are useful for treating neoplastic disease caused by oncogenic viruses. The term "thiadiazolin-3,5-dione compound" as used herein refers to compounds having the following backbone.

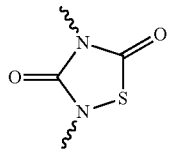

As noted by a ᨆ , the nitrogen atoms of this backbone are also bound to additional substituents, thereby resulting in a stable chemical compound. In one embodiment, at least one of the nitrogen atoms of this backbone is bound to a bulky substituent. "Bulky substituent" as used herein refers to a chemical group that interferes with the ability of the viral oncoprotein to bind to the LxCxE motif of a pRb/E2F complex. In one embodiment, the bulky substituent is an optionally substituted aryl, optionally substituted heterocycle, optionally substituted heteroaryl, optionally substituted alkyl, or optionally substituted cycloalkyl. In another embodiment, the bulky substituent is an optionally substituted aryl. In a further embodiment, the bulky substituent is an optionally substituted phenyl.

In one embodiment, the thiadiazolin-3,5-dione compound has the structure noted in formula (I):

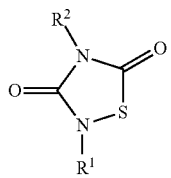

(I)

In this structure, $R^1$ is selected from among optionally substituted aryl, optionally substituted heteroaryl, and optionally substituted heterocycle. In one embodiment, $R^1$ is

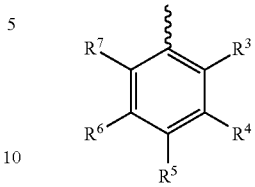

and $R^3$ to $R^7$ are, independently, selected from among H, optionally substituted alkyl, halogen, optionally and substituted alkoxy. In another embodiment, $R^1$ is

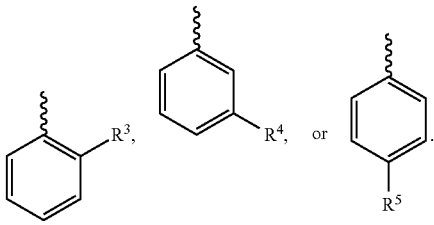

In a further embodiment, $R^1$ is

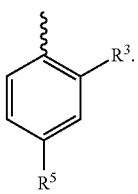

In still another embodiment, $R^1$ is any of these above-noted $R^3$-$R^7$ containing structures and one of $R^3$ to $R^7$ is alkyl or alkoxy. In yet a further embodiment, $R^1$ is any of these above-noted $R^3$ or $R^7$ containing structures and $R^3$ or $R^7$ is alkyl. In another embodiment, $R^1$ is any one of these above-noted $R^4$ or $R^6$ containing structures and $R^4$ or $R^6$ is alkyl. In still a further embodiment, $R^1$ is selected from among

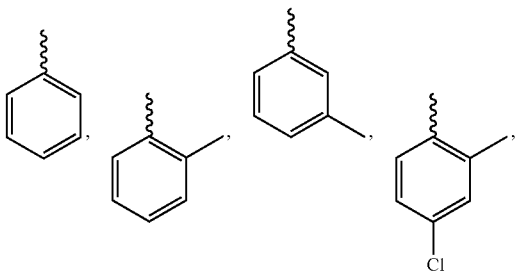

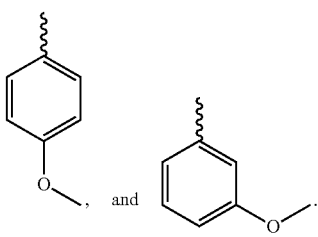

$R^2$ in formula (I) is selected from among optionally substituted alkyl, optionally substituted cycloalkyl, and optionally substituted aryl. In one embodiment, $R^2$ is $C_1$ to $C_6$ alkyl. In another embodiment, $R^2$ is methyl, ethyl, or propyl. In a further embodiment, R² is optionally substituted aryl. In yet another embodiment, R² is

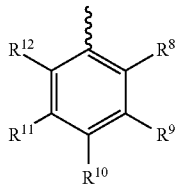

and R⁸ to R¹² are, independently, selected from among H, optionally substituted alkyl, halogen, and optionally substituted alkoxy. In a further embodiment, R² is

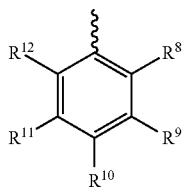

and R⁸, R⁹, R¹¹, and R¹² are H and R¹⁰ is alkoxy. In still another embodiment, R² is

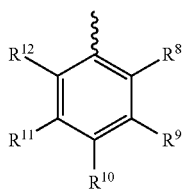

and R¹⁰ is OCH₃.

In another embodiment, the thiadiazolin-3,5-dione compound is:

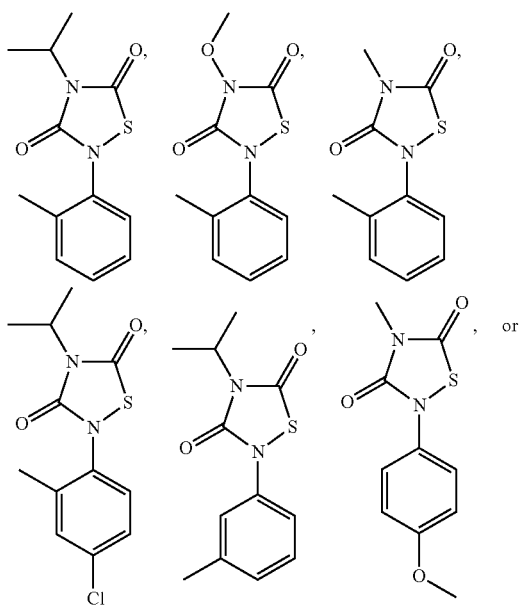

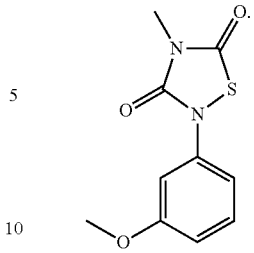

An "alkyl" group as used herein refers to saturated aliphatic hydrocarbon groups. An alkyl may have straight- or branched-chains. In one embodiment, an alkyl group has 1 to about 10 carbon atoms (i.e., $C_1$, $C_2$, $C_3$, $C_4$, $C_5$ $C_6$, $C_7$, $C_8$, $C_9$, or $C_{10}$), or ranges there between. In another embodiment, an alkyl group has 4 to about 10 carbon atoms (i.e., $C_4$, $C_5$, $C_6$, $C_7$, $C_8$, $C_9$, or $C_{10}$), or ranges there between. In a further embodiment, an alkyl group has 5 to about 10 carbon atoms (i.e., $C_5$, $C_6$, $C_7$, $C_8$, $C_9$, or $C_{10}$), or ranges there between.

A "cycloalkyl" group as used herein refers to saturated aliphatic hydrocarbon groups which are cyclic. In one embodiment, a cycloalkyl has 3 to about 10 carbon atoms (i.e., $C_3$, $C_4$, $C_5$, $C_6$, $C_7$, $C_8$, $C_9$, or $C_{10}$), or ranges there between. In another embodiment, a cycloalkyl has 5 to about 10 carbon atoms (i.e., $C_5$, $C_6$, $C_7$, $C_8$, $C_9$, or $C_{10}$), or ranges there between.

The terms "substituted alkyl" and "substituted cycloalkyl" refer to alkyl and cycloalkyl groups, respectively, having one or more substituents including, without limitation, hydrogen, halogen, CN, OH, NO₂, amino, aryl, heterocyclic, heteroaryl, alkoxy, and aryloxy.

"Alkoxy" refers to the group R—O— where R is an alkyl group, as defined above. Exemplary $C_1$-$C_6$ alkoxy groups include but are not limited to methoxy, ethoxy, n-propoxy, i-propoxy, n-butoxy and t-butoxy.

The term "substituted alkoxy" refers to an alkoxy group having one or more substituents on the alkyl chain including, without limitation, hydrogen, halogen, CN, OH, NO₂, amino, aryl, heterocyclic, heteroaryl, alkoxy, and aryloxy.

"Aryloxy" refers to the group R—O— where R is an aryl group, as defined below.

The term "substituted aryloxy" refers to an aryloxy group having one or more substituents on the alkyl chain or aryl moiety including, without limitation, hydrogen, halogen, CN, OH, NO₂, amino, aryl, heterocyclic, heteroaryl, alkoxy, and aryloxy.

The terms "substituted alkyl" and "substituted cycloalkyl" refer to alkyl and cycloalkyl groups, respectively, having one or more substituents including, without limitation, hydrogen, halogen, CN, OH, NO₂, amino, aryl, heterocyclic, heteroaryl, alkoxy, and aryloxy.

The term "halogen" as used herein refers to Cl, Br, F, or I groups.

The term "aryl" as used herein refers to an aromatic, carbocyclic system, e.g., of about 6, 7, 8, 9, 10, 11, 12, 13 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, NO$_2$, amino, alkyl, cycloalkyl, aryloxy, alkoxy, aryl, or heteroaryl. Desirably, a substituted aryl group is substituted with 1, 2, 3, or 4 groups.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6, 7, 8, 9, 10, 11, 12, 13 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1, 2, 3, 4, or 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5, 6, 7, 8, 9, 10, 11, 12, 13 to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1, 2, 3, 4 or 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzopyranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, NO$_2$, amino, alkyl, cycloalkyl, aryloxy, alkoxy, aryl, or heteroaryl. A substituted heterocycle or heteroaryl group may have 1, 2, 3, or 4 substituents.

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In one embodiment, pharmaceutically acceptable salts can be formed from organic and inorganic acids. Examples of useful organic and inorganic acids include, without limitation, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In another embodiment, pharmaceutically acceptable salts may also be formed from organic and inorganic bases. Examples of useful inorganic bases include, without limitation, alkali metal salts such as, e.g., sodium, lithium, or potassium, such as alkali metal hydroxides. Pharmaceutically acceptable salts may also be formed from organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmonoethanolammonium, diethanolamine, ethylenediamine, and the like. In one example, the base is selected from among sodium hydroxide, lithium hydroxide, potassium hydroxide, and mixtures thereof.

These salts, as well as other compounds, can be in the form of esters, carbamates, i.e., "pro-drugs", which convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons, 1996, which is herein incorporated by reference.

The compounds discussed herein also encompass "metabolites" which form by in vivo processing of the compounds.

II. Administration of the Thiadiazolin-3,5-dione Compounds

A. Compositions

The compounds of the invention may be formulated neat or with one or more excipient for administration. One of skill in the art would readily be able to determine suitable excipients based on the selected thiadiazolin-3,5-dione compound, patient, administration route, disease/condition being treated, among others. Not only may the composition be solid or liquid, but excipient(s) may be solid and/or liquid carriers. The carriers may be in dry or liquid form and must be pharmaceutically acceptable. The compositions are typically sterile solutions or suspensions.

Suitably, the thiadiazolin-3,5-dione compounds may be formulated for delivery to a patient by any suitable route including, e.g., transdermal, mucosal (intranasal, buccal, vaginal), oral, parenteral, intravenous, intratumoral, intranodal, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the thiadiazolin-3,5-dione compounds may be combined with one or more excipients. Examples of excipients which may be combined with the thiadiazolin-3,5-dione compound include, without limitation, solid carriers, liquid carriers, adjuvant, antioxidants, suspending agent, syrup, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, thickening agents, or viscosity regulators. See, the excipients in "Handbook of Pharmaceutical Excipients", $5^{th}$ Edition, Eds.: Rowe, Sheskey, and Owen, APhA Publications (Washington, D.C.), 2005 and U.S. Pat. No. 7,078,053, which are incorporated herein by reference. The selection of the particular excipient is dependent on the nature of the thiadiazolin-3,5-dione compound selected and the particular form of administration desired.

When the route of administration is oral, the composition may be any suitable conventional form, including, without limitation, the form of a capsule, caplet, gel tab, dispersible powder, granule, suspension, liquid, thin film, chewable tablet, rapid dissolve tablet, medical lollipop, or fast melt. In one embodiment, the composition is a liquid. In a further embodiment, the composition is a solid. In another embodiment, the composition is a suspension. One of skill in the art would readily be able to formulate the compositions discussed herein in any one of these forms.

Solid carriers include, without limitation, starch, lactose, dicalcium phosphate, microcrystalline cellulose, sucrose and kaolin.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

Liquid carriers may be utilized in preparing solutions, suspensions, emulsions, syrups and elixirs. In one embodiment, the thiadiazolin-3,5-dione compound is dissolved a liquid carrier. In another embodiment, the thiadiazolin-3,5-dione compound is suspended in a liquid carrier. In one embodiment, the liquid carrier includes, without limitation, water, e.g., sterile water, organic solvents (such as glycerol, propylene glycol, liquid polyethylene glycol, dimethylsulfoxide (DMSO)), oils (such as fractionated coconut oil, arachis oil, corn oil, peanut oil, and sesame oil and oily esters such as ethyl oleate and isopropyl myristate), fats, cellulose derivatives such as sodium carboxymethyl cellulose, and non-ionic surfactants.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the thiadiazolin-3,5-dione compound may be combined with a suspending agent, including about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5 to about 5% of suspending agent.

In another embodiment, the thiadiazolin-3,5-dione compound may be combined with a syrup containing, e.g., about 10, 15, 20, 25, 30, 35, 40, 45, to about 50% of sugar.

In a further embodiment, the thiadiazolin-3,5-dione compound may be combined with an elixir containing, e.g., about 20, 25, 30, 35, 40, 45 to about 50% ethanol, and the like.

In another embodiment, the compositions may be utilized as inhalants or aerosols. When administered as an inhalant, the compositions may be in fluid unit doses using the thiadiazolin-3,5-dione compound and a vehicle for delivery by an atomizing spray pump or by dry powder for insufflation. When administered as an aerosol, the compositions may be in a pressurized aerosol container together with a gaseous or liquefied propellant, e.g., dichlorodifluoromethane, carbon dioxide, nitrogen, propane, and the like. Also optionally provided is the delivery of a metered dose in one or more actuations. When the compositions are administered intranasally, the administration may be performed using a mist or spray.

The thiadiazolin-3,5-dione compounds may also be administered parenterally or intraperitoneally as solutions, suspensions, dispersions, or the like. Such pharmaceutical preparations may contain, e.g., about 25, 30, 35, 40, 45, 50, 55, 60, 65, 70, 75, 80, 85, to about 90% of the thiadiazolin-3,5-dione compound in combination with the carrier.

The thiadiazolin-3,5-dione compounds may also be administered via a vaginal ring or transdermal patch.

The effective dosage or amount of the thiadiazolin-3,5-dione compounds may vary depending on the particular thiadiazolin-3,5-dione compound employed, the mode of administration and the severity of the condition being treated. In one embodiment, the effective amount is about 0.01 mg/kg to 10 mg/kg body weight. In another embodiment, the effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the effective amount of the thiadiazolin-3,5-dione compound can be determined by the attending physician and depends on the condition treated, the compound administered, the route of delivery, the age, weight, severity of the patient's symptoms and response pattern of the patient.

The effective amount of the thiadiazolin-3,5-dione compound may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses. The number and frequency of dosages corresponding to a completed course of therapy will be determined according to the judgment of a health-care practitioner. The effective amounts described herein refer to total amounts administered for a given time period; that is, if more than one thiadiazolin-3,5-dione compound or a pharmaceutically acceptable salt thereof is administered, the effective amounts correspond to the total amount administered.

These dosage regimens may be adjusted to provide the optimal therapeutic response. For example, several divided doses of each component may be administered daily or the dose may be proportionally increased or reduced as indicated by the exigencies of the therapeutic situation. In one embodiment, the compounds or compositions discussed herein may be administered on a daily, monthly, or yearly basis. In one embodiment, daily administration is once. In another embodiment, daily administration includes divided units which are administered over the course of each day.

B. Additional Pharmaceutical Reagents

When utilized for these purposes, the thiadiazolin-3,5-dione compounds can be administered in combination with other pharmaceutical agents, as well as in combination with each other. The term "pharmaceutical" agent as used herein refers to a chemical compound which results in a pharmacological effect in a patient.

The thiadiazolin-3,5-dione compounds described herein can be administered to a patient in need thereof with one or more of these pharmaceutical agents. In one embodiment, the thiadiazolin-3,5-dione compounds are combined with one or more of these pharmaceutical agents, i.e., delivered to the patient concurrently. In another embodiment, the thiadiazolin-3,5-dione compounds are delivered to the patient concurrently therewith one or more of these pharmaceutical 1 agents. In a further embodiment, the thiadiazolin-3,5-dione compounds are delivered prior to one or more of these pharmaceutical agents. In still another embodiment, the thiadiazolin-3,5-dione compounds are delivered subsequent to one or more of these pharmaceutical agents.

In one embodiment, the thiadiazolin-3,5-dione compounds may be administered with a chemotherapeutic. One of skill in the art would readily be able to select a chemotherapeutic for administration with the thiadiazolin-3,5-dione compounds based on the cancer being treated, patient, among others. In one embodiment, the chemotherapeutic is selected from among cisplatin, paclitaxel, topotecan, ifosfamide, or 5-fluorouracil.

The thiadiazolin-3,5-dione compounds may also be administered with a compound which inhibits binding of HPV E6 to p53, i.e., "E6 inhibitor". In one embodiment, the E6 inhibitor compound which inhibits binding of HPV E6 to p53 is selected from among the following compounds. See, Baleja, "Identification of inhibitors to Paillomavirus type 16 E6 protein based on three-dimensional structure of interacting proteins", Antiviral Res., 72(1):49-59 (October, 2006) and D'Abramo and Archambault "Small molecule inhibitors of human papillovavirus protein-protein interactions" Open Virol. J., 5: 80-95 (2011), which are herein incorporated by reference.

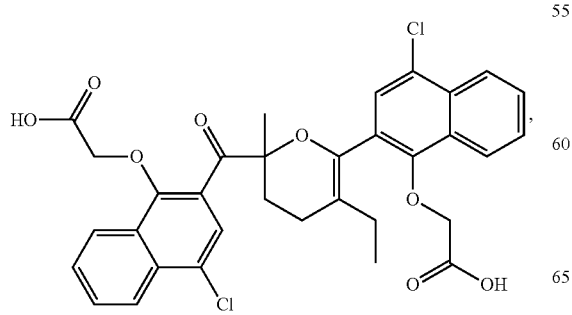

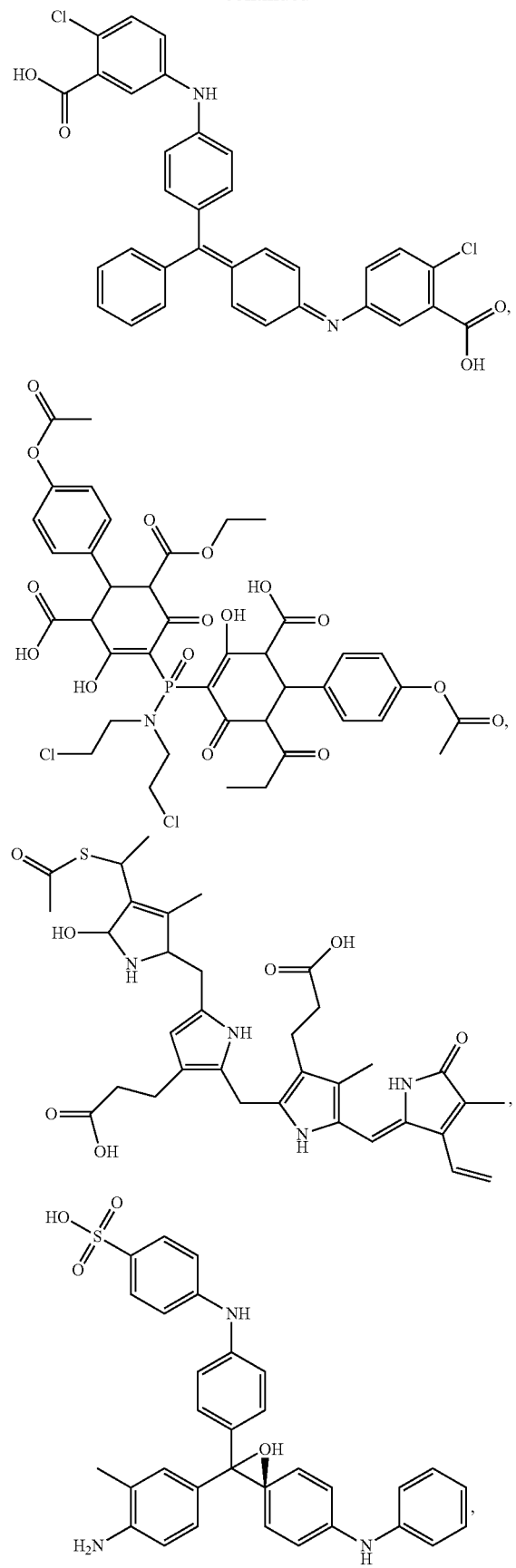

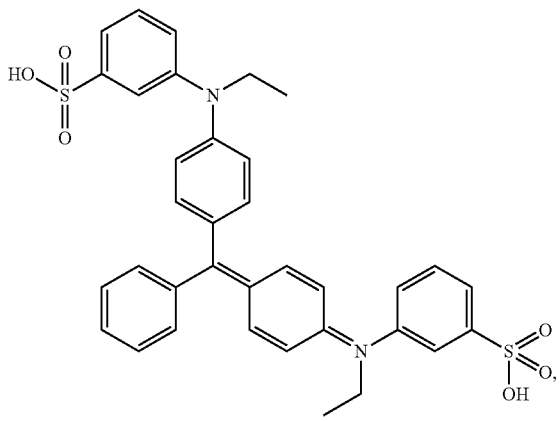

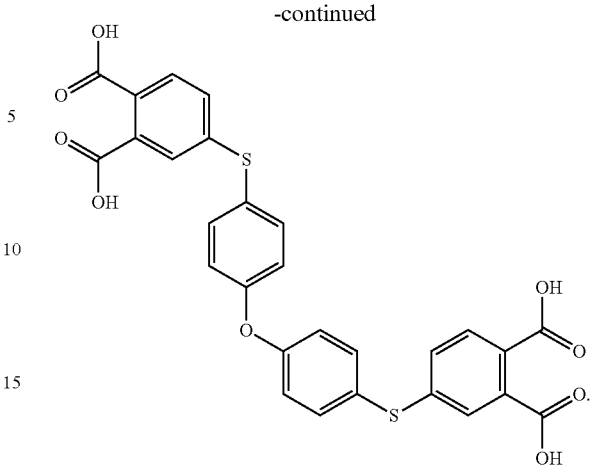

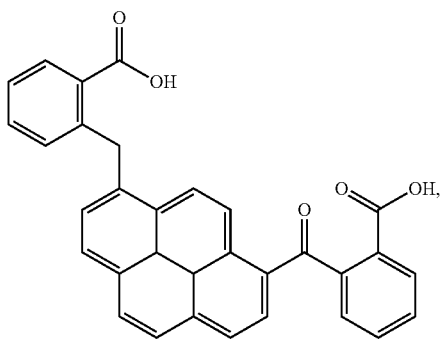

The thiadiazolin-3,5-dione compounds may further be administered concurrently, subsequent, or prior to additional reagents which are utilized for immunotherapy and/or in vaccines. Desirably, the immunotherapy and/or vaccines are tailored to the patient and specific disease/conditions being treated. In one embodiment, the immunotherapy and/or vaccines are tailored to the patient and specific cancer being treated.

C. Additional Treatment Protocols

The thiadiazolin-3,5-dione compounds described herein may be utilized to treat patients afflicted with neoplastic disease by their administration in conjunction with a non-chemical treatment protocol. For example, surgical debulking, in certain embodiments is a necessary procedure for the removal of large tumor masses, and can be employed before, during or after application of the methods and compositions as described herein. Chemotherapy and/or radiation therapy, in other embodiments, bolster the effects of the therapy described herein. Finally, immune-based therapies can eradicate residual disease and activate endogenous immune responses. Such combination approaches (surgery plus chemotherapy/radiation plus immunotherapy) are anticipated to be successful in the treatment of many cancers along with the methods described herein.

Still other adjunctive therapies for use with the methods and compositions described herein include, in one embodiment, acupuncture. In a further embodiment, the non-chemical treatment protocol is surgery. In yet another embodiment, the non-chemical treatment protocol is chiropractic care. In still another embodiment, the non-chemical treatment protocol is passive or active immunotherapy. In a further embodiment, the non-chemical treatment protocol includes X-rays. In still another embodiment, the non-chemical treatment protocol includes ultrasounds, among others. Still other method steps that can be included with or adjunctive to the methods described herein are diagnostic assessments, e.g., blood testing, to determine or monitor the progress of the infection, the course or status of the disease, relapse or any need for booster administrations of the compositions.

III. Kits Containing the Thiadiazolin-3,5-Dione Compounds

Also provided are kits or packages of pharmaceutical formulations containing (i) the thiadiazolin-3,5-dione compound discussed above and used herein; and (ii) a compound which inhibits binding of HPV E6 to p53. In one embodiment, the thiadiazolin-3,5-dione compound is a compound of formula (I). Suitably, the kits contain one or more thiadiazolin-3,5-dione compounds as described herein and one or more compound which inhibits binding of HPV E6 to p53. Advantageously, for use in the kits, the thiadiazolin-3,5-dione compound and compound which inhibits binding of HPV E6 to p53 are formulated for the desired delivery vehicle and route. For example, the thiadiazolin-3,5-dione compound and compound which inhibits binding of HPV E6 to p53 can be formulated for oral delivery, parenteral delivery, vaginal ring, transdermal delivery, or mucosal delivery as discussed in detail above.

In one embodiment, the kit is designed for delivery at home. The kit may, therefore, include tubes or other containers, applicators, needles, syringes, and other appropriate packaging and instructions for use.

IV. Embodiments of the Methods

In one embodiment, a method for preventing disruption of pRb/E2F complexes is provided and includes administering a compound of formula (I) to a patient in need thereof.

In another embodiment, a method for preventing disruption of pRb/E2F complexes is provided and includes administering, to a patient in need thereof, a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In a further embodiment, a method for preventing interaction between pRb and a viral oncoprotein is provided and includes administering a compound of formula (I) to a patient in need thereof.

In yet another embodiment, a method for preventing interaction between pRb and a viral oncoprotein is provided and includes administering, to a patient in need thereof, a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In still a further embodiment, a method for preventing or a disease caused by a virus carrying a viral oncoprotein containing a L×C×E motif is provided and includes administering a compound of formula (I) to a patient in need thereof In another embodiment, a method for preventing or a disease caused by a virus carrying a viral oncoprotein containing a L×C×E motif is provided and includes administering, to a patient in need thereof, a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In yet a further embodiment, a method for preventing or treating neoplastic disease is provided and includes administering a compound of formula (I) to a patient in need thereof.

In still another embodiment, a method for preventing or treating neoplastic disease is provided and includes administering, to a patient in need thereof, a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In a further embodiment, a method for preventing HPV-E7 mediated E2F displacement from pRb is provided and includes administering a compound of formula (I) to a patient in need thereof.

In yet another embodiment, a method for preventing HPV-E7 mediated E2F displacement from pRb is provided and includes administering a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In still a further embodiment, a method for disrupting pRb/HPV-E7 complexes is provided and includes administering a compound of formula (I) to a patient in need thereof.

In another embodiment, a method for disrupting pRb/HPV-E7 complexes is provided and includes administering a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In yet a further embodiment, a method for preventing or treating genital warts is provided and includes administering a compound of formula (I) to a patient in need thereof.

In still another embodiment, a method for preventing or treating genital warts is provided and includes administering a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In a further embodiment, a method for preventing or treating neoplastic disease caused by human papilloma virus, adenovirus, or SV40 is provided and includes administering a compound of formula (I) to a patient in need thereof.

In yet another embodiment, a method for preventing or treating neoplastic disease caused by human papilloma virus, adenovirus, or SV40 is provided and includes administering a composition containing (i) a thiadiazolin-3,5-dione compound comprising an optionally substituted aryl group bound to one nitrogen atom of the thiadiazolin-3,5-dione compound; and (ii) a compound which inhibits binding of HPV E6 to p53.

In any of the above methods, the selected compound may be formulated as described above and administered via a route and in a dosage that is deemed suitable by one of skill in the art, taking into consideration the specific disease, the physical condition and status of the patient and any other relevant clinical symptoms.

The following examples are illustrative only and are not intended to limit the present invention.

EXAMPLES

Example 1

Analysis, Cultures, and Reagents (i) Spectroscopic Analyses

Liquid Chromatography-Mass Spectral (LC-MS) analysis of the compounds discussed in the examples was performed using a Waters Micromass® ZQ™ system. The mobile phase contained 0.5% formic acid in $H_2O$ and acetonitrile. The compounds were resolved on a Waters Sunfire™ C18 4.6×50 mm analytical column at a flow rate of 2.0 mL/min with a gradient of 10% to 90% acetonitrile over 6 minutes followed by 1 minute of 100% acetonitrile. Percent purity was calculated based on the UV absorption chromatogram.

$^1$H-Nuclear Magnetic Resonance (NMR) analysis of the compounds discussed herein was performed on a Bruker AMX-500 spectrometer. Chemical shifts are reported as δ values relative to internal chloroform (δ 7.27).

(ii) Cell Cultures

C-33A and SiHa cell lines (ATCC Nos. HTB-31™ and HTB-35™ ATCC cell lines) and grown in 1× minimal eagle's media (MEM, Cellgro) supplemented with fetal bovine serum (10%; Hyclone), penicillin-streptomycin (10 μg/mL; Cellgro), L-glutamine (2 mM; Cellgro), sodium pyruvate (1 mM; Cellgro), and non-essential amino acids (100 μM; Gibco). HeLa and HCT116 cell lines (ATCC Nos. CCL-2™ and CCL-247™ cell lines) were generous gifts from the laboratories of Susan Janicki, and Meenhard Herlyn, respectively, and maintained in the same way.

(iii) Expression and Purification of Proteins

The DNA encoding HPV16-E7$_{CR2-3}$ (residues 17-98 of SEQ ID NO: 1 (NCBI sequence #2002324A)), HPV1A-E7$_{CR2-3}$ (residues 16-93 of SEQ ID NO: 4 (NCBI sequence #NP_040307)) and Ad5-E1A$_{CR1-3}$ (residues 36-189 of SEQ ID NO: 2 (NCBI sequence #AP_000197)) were cloned into the pRSET vector, containing an N-terminal 6×-histidine tag. E. coli BL21(DE3) cells (Catalog No. 200131, Stratagene) transformed with these modified pPRSET vectors were grown to an OD$_{600}$ of 0.3 at 37° C. The temperature was reduced to 25° C. for HPV-E7 expressing cells and to 18° C. for Ad5-E1A expressing cells, and the cells were induced with IPTG (1 mM) at an OD$_{600}$ of 0.5-0.7 and grown overnight. Following protein expression, the cells were centrifuged and frozen at −80° C. prior to purification. Cells were resuspended and lysed by sonication in a buffer containing Tris (20 mM), pH=7.5, NaCl (500 mM), imidazole (35 mM), Zn(OAc)$_2$ (10 μM), BME (10 mM) and 1× PMSF. The cell lysate was centrifuged at 18,000 RPM and the resulting supernatant was loaded onto a Ni-NTA column pre-equilibrated with Tris (20 mM), pH=7.5, NaCl (500 mM), imidazole (35 mM), Zn(OAc)$_2$ (10 μM), and BME (10 mM). The column was washed and the bound protein was eluted using an imidazole gradient (35 mM to 250 mM). Fractions containing protein were concentrated and further purified using size exclusion chromatography on a Superdex™ 200 analytical column (GE Healthcare Life Sciences) in a buffer containing Tris (20 mM), pH=7.5, NaCl (150 mM), and BME (10 mM).

For the use of pRb in the ELISA assay, DNA encoding pRb$_{ABC}$ (residues 376-928 of SEQ ID NO: 3 (NCBI sequence #P06400)) were cloned into the pFAST-Bac vector, containing an N-terminal GST tag. Protein was expressed in Sf9 cells for 48 hours before harvesting. The protein was purified as described by the manufacturer (Novagen). The plasmid pGex6P-1-E2F1, encoding the marked-box and transactivation domain of E2F1 (residues 243-437 of SEQ ID NO: 5 (NCBI Accession #NP_005216)) with an N-terminal GST tag, was provided by Dr. Steven Gamblin (MRC, Mill Hill, UK). GST-E2F1$_{MB-TA}$ was expressed in E. coli BL21(DE3) CodonPlus® RIL cells (Novagen) for 5-6 hours at 30° C. and purified as described in Liu et al., J Biol Chem 281:578-586 (2006). The GST tag was removed using PreScission® Protease reagent (GE Healthcare Life Sciences) as described in Liu et al., 2006 to yield an untagged E2F1$_{MB-TA}$ for assay purposes (Liu et al., 2006).

For use in pull-down studies, GST-tagged full-length HPV-E7 was cloned into the pGEX-4T-1 vector, expressed in E. coli BL21(DE3) cells, and purified as described by the manufacturer (Novagen). 6×His-pRb$_{ABC}$ (residues 376-928 of SEQ ID NO: 3 (NCBI sequence #P06400)) was cloned into the pRSET vector, expressed and purified as described above for the 6×His-tagged proteins, except that Zn(OAc)$_2$ was excluded from the buffers.

For use in isothermal titration calorimetry studies, untagged pRb$_{AB}$ (372-787 with the linker from 590-635 removed) was prepared as described in Xiao et al., PNAS USA, 100:2363-2368 (2003).

Example 2

Screening and Identification of pRb Antagonists (i) Compound Libraries

Approximately 88,000 compounds from several diverse small molecule libraries were screened using the ELISA-based assay. Two thousand compounds comprising the Spectrum Collection from MicroSource Discovery Systems (Gaylordsville, Conn.) were tested at a final concentration of 8.3 μM. A library of 14,400 chemically diverse compounds from Maybridge HitFinder™ library (Cambridge, UK) was tested at a final concentration of 12.5 μM. A third set of compounds, comprising 71,539 small molecules, from the orthogonally pooled screening (OPS) libraries, provided by the Lankenau Chemical Genomics Center (Wynnewood, Pa.) were tested at a final concentration (6.25 μM to 12.5 μM). The HitFinder™ and OPS libraries were orthogonally compressed to contain 5 or 10 compounds per well, respectively, and the data were deconvoluted based on methods similar to those described in Devlin et al., Drug Development Research, 37(2):80-85 (February, 1996); Ferrand et al., Assay Drug Dev Technol 3:413-424 (2005); and Motlekar et al., Assay Drug Dev Technol 6:395-405 (2008).

The protein constructs employed were 6×His-HPV16-E7$_{CR2-3}$ (residues 17-98 of SEQ ID NO: 1 (NCBI sequence #2002324A)) harboring the L×C×E motif of HPV-E7, GST-pRb$_{ABC}$ (residues 376-928 of SEQ ID NO: 3 (NCBI sequence #P06400)) harboring the A/B pocket domain and C-terminal region of pRb and untagged E2F$_{MB-TA}$ (residues 243-437 of SEQ ID NO: 5 (NCBI Accession #NP_005216)) containing the marked-box and transactivation domains of E2F that make pRb contact. 6×His-HPV16-E7$_{CR2-3}$ was modified to improve its solubility and reduce its tendency to aggregate by substituting nonconserved cysteine residues with those found in low-risk HPV1A-E7.

(ii) High Throughput Solution Screening and Data Processing

The assay employed an enzyme-linked immunosorbance assay (ELISA) performed as follows. In brief, the GST-pRb$_{ABC}$/E2F$_{MB-TA}$ complex was attached to a glutathione-coated 384-well microtiter plate and 6×His-HPV16-E7$_{CR2-3}$ in the presence of either 1% DMSO (negative control) or 10 μM compound dissolved in DMSO. Inactive compounds had no effect on HPV-E7 binding to pRb, which prevented formation of pRb/E2F complexes. This resulted in unbound E2F, which was removed by another wash step. Compounds that inhibited HPV-E7-mediated disruption of pRb/E2F complexes maintain E2F bound to the plate through pRb. Therefore, following plate washing, the amount of E2F remaining bound to the plate was a measure of the potency of the compound in inhibiting HPV-E7-mediated disruption of pRb/E2F complexes. The amount of E2F remaining bound to the plate was quantified by a bioassay using a primary anti-E2F1 antibody. This was followed by a secondary antibody linked to horseradish peroxidase that acts on the ELISA Pico Chemiluminescent substrate, which was detected using an ultrasensitive-luminometer detector.

The linear range of the assay was first determined by titration experiments measuring the amount of E2F remaining bound after incubation of the GST-pRb$_{ABC}$/E2F$_{MB-TA}$ complex with serial dilutions of E7.

The screen was performed using automation in 384-well microtiter plates in screening buffer (20 mM Tris, pH=7.5, 150 mM NaCl and 0.05% Tween20). First, a complex was formed between 100 ng/100 μL GST-pRb$_{ABC}$ and 10 ng/100 μL E2F$_{MB-TA}$ that was incubated for 30-60 minutes. At the same time, 20 μL of 500 nM 6×His-HPV16-E7$_{CR2-3}$ was added to a 384-well plate (Fisher Scientific) containing test compound (0.5 μL) dissolved in DMSO (or DMSO control) and allowed to incubate for 30-60 minutes. Forty μL of GST-pRb$_{ABC}$/E2F$_{MB-TA}$ complex was then added to each well containing 6×His-HPV16E7$_{CR2-3}$ and test compound, and incubated at room temperature for an additional 30-60 minutes. Fifty μL of the GSTpRb$_{ABC}$/E2F$_{MB-TA}$-16E7$_{CR2-3}$ mixture was then transferred to a pre-washed glutathione-coated 384-well plate (Thermo Scientific) and allowed to shake for 30 minutes. The plate was then washed with the screening buffer and primary anti-E2F1 antibody (50 μL, Millipore) diluted 1:25,000 was added to each well and incubated for 60 minutes on a shaker. The plate was washed again and a goat anti-mouse IgG horseradish peroxidase antibody (50 μL; BioRad) diluted 1:5,000 was added and incubated for 30 minutes on the shaker. After another set of washes, 50 μL of a 50:50 mixture of ELISA Pico Chemiluminescent Substrate (Pierce) was added to each well and read within 20 minutes using an Envision® plate-reader (Perkin Elmer). The Janus® Automated Workstation (Perkin Elmer) was used for liquid handling in an automated HTS protocol.

Each plate receiving test compound also contained positive controls: GST-pRb$_{ABC}$/E2F$_{MB-TA}$+DMSO in columns 1 and 23 and negative controls GST-pRb$_{ABC}$/E2F$_{MB-TA}$+16E7$_{CR2-3}$/DMSO in columns 2 and 24. Uniformity plates (192 positive controls, and 192 negative controls) were distributed throughout the screening plates to ensure both assay and result reliability. All compounds were screened in duplicate.

The Z' factor parameter was used to assess the robustness of the assay during automation in a 384-well format. The chemiluminescence signal from each well was normalized to the negative controls on each plate based on the following equation:

$$Z=(\chi-\mu)/\sigma$$

$\chi$=chemiluminescence signal of a given well
$\mu$=mean of the negative control population
$\sigma$=standard deviation of the negative control population Generally, compounds giving a chemiluminescence signal higher than 3 standard deviations above the mean were considered hits. Software applications developed by CeuticalSoft (OpenHTS® depository) were used to deconvolute the orthogonally compressed data for both the HitFinder® and OPS libraries. The data was grouped into four categories:

i. actives: compounds that displayed >50% inhibition of E2F displacement and clearly mapped to a unique well in both the horizontal and vertical directions)
ii. ambiguous: compounds that mapped to two or more wells in either dimension
iii. orphan: compounds that displayed inhibition in only one direction
iv. inactives: compounds that displayed no inhibition A three day replicate plate experiment consistently yielded Z'-factors between 0.62 and 0.71 indicating that the assay was sufficiently robust for valid drug screening (Zhang, 1999 cited above). This screen identified 364 small molecule HPV-E7 inhibitors, yielding a primary screen hit rate of 0.41%, based on their effect of producing a luminescence signal greater than three standard deviations from the mean value. These compounds were selected and tested to confirm their activities and measure potency values. One hundred twenty of these 364 compounds had IC$_{50}$ values of 15.6 μM or lower using the same assay format as the primary screen, reducing the hit rate to 0.14%. The remaining compounds either did not show reproducible inhibition, or were not sufficiently potent to determine their IC$_{50}$ value and were discarded from further analyses.

The 120 confirmed "actives" were then tested in secondary assays as described below to identify those with apparently selective pharmacological activity in cells. A summary of the process for the identification of confirmed screening hits is shown in FIG. 1.

(iii) Cytotoxicity in Cervical Cancer Cells

These 120 compounds were then analyzed for cytotoxicity in cervical cancer cells either infected with HPV16 (SiHa) or negative for infection with HPV (C-33A) (Yee et al., 1985). The metabolic viability of cells was measured using a MTS assay (3-(4,5-dimethylthiazol-2-yl)-5-(3-carboxymethoxyphenyl)-2-(4-sulfophenyl)-2H-tetrazolium).

Cultured cell lines were seeded in 384-well, clear, tissue culture plates (NUNC) at 10,000 cells/well and 1,000 cells/well for C-33A and SiHa, respectively, and maintained overnight. These concentrations were determined based on each cell line's doubling time. The next day, the compounds were independently dissolved in media (25 μM to 100 nM) to a final DMSO concentration of 0.5%, were added to each well and incubated with cells for 48 hours. Cell viability was then monitored by addition of MTS reagent (8 μL; Promega) and measurement at A$_{490}$ using a Wallac Envision™ plate reader after 3 hours of incubation.

Staurosporine, which has the following structure and is a non-specific kinase inhibitor, was used as a positive control because it was expected to be toxic in all cells (Ruegg and Burgess, 1989).

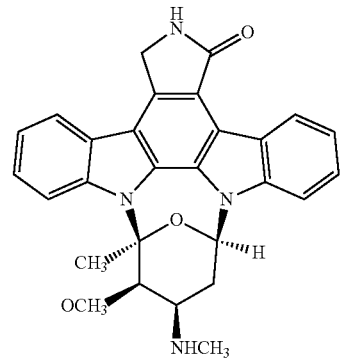 [SMILES: CN[C@@H]1C[C@H]2O[C@@](C)([C@@H]1OC)n1c3ccccc3c3c4c(c5c6ccccc6n2c5c31)C(=O)NC4]

Staurosporine

Out of the 120 compounds tested, 25 were selectively cytotoxic in SiHa cells (HPV 16) and not in C-33A (HPV negative) cells at concentrations at or below 6 Of the 25 compounds that were selectively toxic in SiHa cells, 7 had $IC_{50}$ values that ranged from 0.34 to 7.6 μM (FIG. 2A and Table 1).

The increase in apoptosis in SiHa cells upon treatment with the thiadiazolin-3,5-dione compounds illustrate that the thiadiazolin-3,5-dione compounds antagonize the ability of E7 to control the proliferation of the HPV-positive cell lines.

TABLE 1

| Compound | Structure | Purity (%) | Retention Time (min) |
|---|---|---|---|
| 1 | (structure: N-isopropyl, N'-(2-methylphenyl) thiadiazolin-3,5-dione) | 92.7 | 4.27 |
| 2 | (structure: N-methoxy, N'-(2-methylphenyl) thiadiazolin-3,5-dione) | 89.8 | 4.17 |
| 3 | (structure: N-methyl, N'-(2-methylphenyl) thiadiazolin-3,5-dione) | 80.5 | 3.58 |
| 4 | (structure: N-isopropyl, N'-(4-chloro-2-methylphenyl) thiadiazolin-3,5-dione) | 94.7 | 4.67 |
| 5 | (structure: N-isopropyl, N'-(3-methylphenyl) thiadiazolin-3,5-dione) | 96.8 | 4.50 |
| 6 | (structure: N-methyl, N'-(4-methoxyphenyl) thiadiazolin-3,5-dione) | 91.2 | 3.15 |
| 7 | (structure: N-methyl, N'-(3-methoxyphenyl) thiadiazolin-3,5-dione) | 97.8 | 3.18 |

(iv) Cytotoxicity in Cells Other than Cervical Cancer Cells

To eliminate the possibility that the seven thiadiazolin-3,5-dione compounds identified above (Table 1) were cytotoxic to SiHa cells due to their role in inactivating pRb, which is mutated in C-33A cells, they were tested in additional cell lines TC-1, a mouse epithelial line co-transformed with HPV 16 E6/E7 and c-Ha-Ras, HeLa, a human cell line infected with HPV 18 and HCT116, a human HPV negative colorectal carcinoma cell line containing an intact retinoblastoma gene (DeFilippis et al., 2003; Scheffner et al., 1991; Yee et al., 1985).

Cultured cell lines were seeded in 384-well, clear, tissue culture plates (NUNC) at 10,000 cells/well, 1,000 cells/well, 1,000 cells/well, 1,000 cells/well, and 2,000 cells/well for C-33A, SiHa, HeLa, TC-1, or HCT116 cells, respectively, and maintained overnight. These concentrations were determined based on each cell line's doubling time. The next day, compounds 1-9 independently dissolved in media to a final DMSO concentration of 0.5%, were added to each well and incubated with cells for 48 hr. Cell viability was then monitored by addition of MTS reagent (8 μL; Promega) and measurement at $A_{490}$ using a Wallac Envision™ plate reader after 3 hours of incubation.

As shown in FIG. 2B, the compounds were not cytotoxic in the HCT116 cell line, were cytotoxic in TC-1 cells, and were moderately cytotoxic in HeLa cells. Taken together, this data suggests that the seven thiadiazolin-3,5-dione compounds identified in the primary MTS are selectively cytotoxic in HPV infected cervical cancer cell lines.

Example 3

Inhibition of HPV-E7 Activity

Since HPV-E7 interacts with both pRb and E2F for disruption of the pRb/E2F complex, the ability of the seven compounds from Example 2 were tested for this ability to inhibit HPV-E7 activity by directly disrupting HPV-E7 interactions with pRb (Liu et al., 2006).

(i) ELISA Assay

An ELISA assay was utilized with modifications such that the amount of 6×His-HPV16-E7$_{CR2-3}$ remaining bound to the partner protein on the plate could be measured. The compounds identified in Example 2 were purchased (Lankenau Institute for Medical Research) as powders. Their purity was verified by LC/MS and their structures by NMR. IC$_{50}$ values were then measured for (i) the compounds identified in Example 1, (ii) the compounds prepared according to Examples 3-5, (iii) 2-phenyl-4-methyl-1,2,4-thiadiazolidin-3,5-dione (available from Molport, Latvia), and (iv) 4-benzyl-2-methyl-1,2,4-thiadiazolidin-3,5-dione (TDZD-8; Catalog No. T8325-5MG, Sigma) using the same ELISA-based assay as described for the high-throughput screen, except that the assay was performed manually in 96-well format and so all volumes used were double those from 384-well format.

All compounds were solubilized in DMSO (50 mM) and diluted for use in the ELISA-based assay at a final DMSO concentration of less than 5%. Ten-fold dilutions of thiadiazolin-3,5-dione compound (starting at 100 μM) were added to a mixture containing GST-pRb$_{ABC}$ and 6×His-HPV16E7$_{CR2-3}$. The amount of E7 remaining was determined by adding a primary anti-His antibody. The concentrations of the compounds in the IC$_{50}$ experiment spanned the range of enzyme activity from no inhibition to complete inhibition. Three independent IC$_{50}$ measurements were performed for each compound and the average and standard deviation values are reported. All data was imported into the GraphPad® Software (Prism) for IC$_{50}$ determination. To calculate the IC$_{50}$ values, the dose-response curves were fit to one-site (Hill slope=1) sigmoidal-dose-response curves.

These data show that increasing the amount of compound led to a displacement of 6×His-HPV16-E7$_{CR2-3}$ from GST-pRb$_{ABC}$, suggesting the compounds prevent the interaction between these two proteins (FIG. 3A).

(ii) Pull-Down Assays

To eliminate potential artifacts from this assay format, the ability of the thiadiazolin-3,5-dione compounds to disrupt HPV-E7/pRb interaction was analyzed by performing pull-downs on Ni-NTA beads using His-pRb$_{ABC}$ and GST-16E7$_{FL}$.

Ten μg His-tagged protein pRb$_{ABC}$ was incubated with 10 μL Ni-NTA beads (Fisher) in a buffer containing Tris (20 mM), pH=7.5, NaCl (150 mM), imidazole (35 mM) and Tween20® reagent (0.05%) for 15 minutes to allow the protein to bind. An equimolar amount of GST-HPV16-E7$_{FL}$ was then added. Compounds 1-7, at various concentrations (0 μM, 0.01 μM, 0.1 μM, 1 μM, 10 μM, and 100 μM), were independently added to each reaction mixture and allowed to incubate at 4° C. for one hour with gentle agitation. After one hour, each set of beads was spun at 500 g, unbound proteins were aspirated and the beads were washed with 1 mL binding buffer (20 mM Tris, pH=7.5, 150 mM NaCl, 35 mM Imidazole and 0.05% Tween20™ reagent). The beads were washed three times with this buffer, and then the beads were subjected to SDS-page analysis. The samples were transferred to PVDF membrane to be visualized by western blotting. Anti-GST mouse monoclonal antibodies (1:2000) (Calbiochem) and anti-His mouse monoclonal antibodies (1:5000) (Fisher) were used. Bands were visualized by chemiluminescence (Pierce) and exposure to film (Kodak). See FIG. 3B.

As was shown using the ELISA method, the pull-down assay showed that an increase in compound concentration lead to a displacement of GST-E7$_{FL}$ from His-pRb$_{ABC}$. The IC$_{50}$ values for the amount of respective compound required for 6×His-HPV16-E7$_{CR2-3}$ displacement from GST-pRb$_{ABC}$, as determined by the ELISA assay, was within ten-fold of the corresponding IC$_{50}$ values of E2F displacement from GST-pRb$_{ABC}$ in the presence of 6×His-HPV16-E7$_{CR2-3}$ (Table 2).

TABLE 2

IC$_{50}$ values for compounds that inhibit HPV-E7-mediated disruption of pRb/E2F and disrupt pRb/viral oncoprotein complexes

|  | 16E7 (500 nM) | 1AE7 (500 nM) | E1A (100 nM) | K$_D$ (μM) | Compound |
|---|---|---|---|---|---|
| pRb/E2F | 7.6 ± 1.2 | 10.6 ± 1.3 | 2.8 ± 2.2 |  | 1 |
| pRb | 11.2 ± 1.3 | 7.9 ± 2.1 | 5.0 ± 1.8 | 0.165 ± 0.052 |  |
| pRb/E2F | 2.2 ± 1.6 | 3.5 ± 1.6 | 0.64 ± 2.3 |  | 2 |
| pRb | 0.57 ± 1.2 | 3.0 ± 2.3 | 2.6 ± 1.3 | 0.104 ± 0.025 |  |
| pRb/E2F | 1.9 ± 1.3 | 4.5 ± 1.7 | 0.24 ± 2.0 |  | 3 |
| pRb | 0.50 ± 1.5 | 3.4 ± 2.0 | 1.0 ± 2.1 | 0.106 ± 0.034 |  |
| pRb/E2F | 3.2 ± 1.3 | 5.5 ± 1.7 | 1.3 ± 2.2 |  | 4 |
| pRb | 4.5 ± 1.5 | 4.7 ± 2.1 | 3.8 ± 1.5 | 0.187 ± 0.022 |  |
| pRb/E2F | 4.6 ± 1.3 | 5.5 ± 1.5 | 1.1 ± 2.5 |  | 5 |
| pRb | 3.2 ± 1.3 | 5.5 ± 2.7 | 3.5 ± 1.7 | 0.210 ± 0.051 |  |
| pRb/E2F | 2.3 ± 1.6 | 3.3 ± 1.6 | 1.7 ± 2.7 |  | 6 |
| pRb | 0.40 ± 1.4 | 1.3 ± 1.3 | 7.7 ± 1.7 | 0.381 ± 0.031 |  |
| pRb/E2F | 0.34 ± 1.9 | 3.5 ± 1.7 | 3.2 ± 2.7 |  | 7 |
| pRb | 0.29 ± 1.7 | 4.0 ± 2.5 | 2.8 ± 2.1 | 0.815 ± 0.070 |  |

Example 7

The Thiadiazolin-3,5-Dione Compounds Function by Binding to pRb Through the LxCxE Binding Motif of Viral Oncoproteins Since HPV-E7 mediates high affinity pRb binding through the association of its LxCxE motif in CR2 to the B domain of pRb, the ability of the thiadiazolidinedione compounds to inhibit the ability of other L×C×E containing viral oncoproteins from disrupting E2F/pRb complexes was tested. The other L×C×E containing viral oncoproteins tested included HPV-E7 from a low risk HPV form (type 1A) and Adenovirus E1A proteins.

A similar ELISA assay was used to assess the ability of the compounds to inhibit the ability of HPV16-E7-mediated disruption of E2F/pRb complexes. For these studies, 6×His-HPV1AE7$_{CR2-3}$ and 6×His-Ad5E1A$_{CR1-3}$, containing the L×C×E motif, were employed. The assay described above was modified in such a way that GST-pRb$_{ABC}$ alone was added to HPV-E7$_{CR2-3}$+ compound, HPV-E7$_{CR2-3}$+DMSO, Ad5-E1A$_{CR1-3}$+ compound, or Ad5-E1A$_{CR1-3}$ DMSO. Mouse monoclonal anti-His antibody (Fisher) diluted 1:10,000 was used to detect how much His-E7$_{CR2-3}$ remained bound to GST-pRb$_{ABC}$ on the plate. Mouse monoclonal Ad5-E1A antibody (Abeam) diluted 1:10,000 was used to detect how much E1A$_{CR1-3}$ remained bound to GST-pRb$_{ABC}$ on the plate. All other steps remained unchanged.

To test the mode of inhibition by the thiadiazolin-3,5-dione compounds, each compound was first incubated with pRb for 30-60 minutes. Different concentrations of HPV-E7$_{CR2-3}$, ranging from 50 µM down to 0.05 µM, were added to the GST-pRb$_{ABC}$+ compound mixture and allowed to incubate for 30-60 minutes. The reaction mixture was then transferred to a glutathione-coated plate, and shaken for 15-20 minutes. Mouse monoclonal anti-His antibody (Fisher) diluted 1:10,000 was used to detect how much HPV-E7$_{CR2-3}$ remained bound to GST-pRb$_{ABC}$ on the plate.

As can be seen in FIG. 4A and Table 2, the compounds show similar levels of inhibition as they did in the presence of 6×His-HPV16E7$_{CR2-3}$. While the IC$_{50}$ values are lower for E1A, this is likely the result of using a lower concentration of E1A that showed linearity in the ELISA assay. The ability of the compounds to prevent an interaction between either 6×His-HPV1AE7$_{CR2-3}$ or 6×His-Ad5E1A$_{CR1-3}$ with GST-pRb$_{ABC}$ was also shown (FIG. 4B). The IC$_{50}$ values from these experiments ranged from 0.2-11.2 µM, which is comparable to the IC$_{50}$ values for compound inhibition of HPV-16E7 mediated inhibition of E2F/pRb complexes (Table 2). This data illustrate that the thiadiazolin-3,5-dione compounds disrupt the interaction between the pRb B domain and the L×C×E motif of the viral oncoproteins.

Example 8

Interaction of the Thiadiazolin-3,5-Dione Compounds with the Structured pRb B Domain This example illustrates the ability of the thiadiazolin-3, 5-dione compounds to bind directly to a truncated pRb protein construct containing the A and B domains of the pRb pocket (pRb$_{AB}$) using isothermal titration calorimetry (ITC).

Binding of compounds 1-9 to pRb$_{AB}$ were measured by ITC using a MicroCal™ VP-ITC isothermal titration calorimeter (MicroCal, Inc). Proteins were extensively dialyzed against a buffer containing Hepes (20 mM), pH=7.5, NaCl (150 mM) and Tris carboxy ethyl phosphine (0.1 mM) prior to analysis. Eight to twelve µL injections of 750-1500 µM compound were titrated into a pRb solution (50-150 µM) pre-equilibrated to 22° C. After subtraction of dilution heats, calorimetric data were analyzed with the MicroCal™ Origin® V5.0 (MicroCal Software, Northampton, Mass.).

The resulting integrated heat-flow spikes confirmed direct binding of thiadiazolin-3,5-dione compounds to pRb with 1:1 stoichiometry and affinities in the sub-micromolar range (FIG. 4C and FIG. 5A). A summary of the dissociation constants is given in Table 2. To further confirm that inhibitor binding was reversible, one of the pRb/thiadiazolin-3,5-dione compound complexes (pRb with compound 478166) was dialyzed overnight and ITC was repeated. As before, a binding curve was obtained yielding a similar dissociation constant and stoichiometry, indicating that the thiadiazolin-3,5-dione compound was still able to interact with pRb in a reversible fashion (FIG. 5B).

These results illustrate that the thiadiazolin-3,5-dione compounds bind directly to pRb. These results also additionally suggest a route for structure-based-drug design of additional HPV inhibitors.

Example 9

Determination of Concentration Thiadiazolin-3,5-Dione Compound Dependence

To deter line if the thiadiazolin-3,5-dione compounds were competitive with HPV-E7 for pRb binding or work through an allosteric mechanism, the ELISA assay was utilized to measure the ability of HPV-E7 to displace E2F from pRb as a function of thiadiazolin-3,5-dione compound concentration. As shown in FIG. 4D, the binding curves for 6×His-HPV16-E7$_{CR2-3}$ mediated displacement of E2F$_{MB-TA}$ from GST-pRb$_{ABC}$ in the presence of varying concentrations of compound 3 (0.025, 0.25, 0.5 and 5.0 µM), were obtained. The calculated K$_d$, i.e., 140, 313, 304 and 764 nM, respectively, were above and below the dissociation constant of pRb (K$_d$ for pRb of 104 nM). The binding curves showed a dependence on the concentration of thiadiazolin-3,5-dione compound, where increasing thiadiazolin-3,5-dione compound concentration is correlated with a rightward shift (higher apparent value) in the IC$_{50}$ values for HPV-E7 mediated displacement of pRb/E2F complex.

These data illustrate that the thiadiazolin-3,5-dione compounds and HPV16-E7 bind competitively to pRb.

Example 10

Effect of the Thiadiazolin-3,5-Dione Compounds on Apoptosis in HPV-Infected Cells Since the thiadiazolin-3,5-dione compounds bind to pRb, data was generated regarding their effect in cells infected with HPV. To perform this example, SiHa cells (infected with HPV16) were employed since the thiadiazolin-3,5-dione compounds were most effective in this cell line. Cells were treated with either DMSO (at a final concentration of 0.5%) or 10 µM of thiadiazolin-3,5-dione compounds 3 and 4, 2-(3,4-dimethyl-phenyl)-4-methyl-1,2,4-oxadiazolin-3,5-dione (which is an inactive oxo analog of compounds 1-7 and is available from Lankenau Institute for Medical Research), or 2 µM of staurosporine, which was shown to be toxic using the MTS proliferation assay, for 48 hours. DNA content was determined by propidium iodine staining and analysis by flow cytometry.

Cultured cell lines were seeded in 60 mm tissue culture dishes (Falcon) at 1×10$^5$ cells/well. The next day, compounds 1-9 (10 µM) or DMSO were added to each dish and allowed to incubate for 48 hours. Cells were then trypsinized, washed with phosphate-buffered saline (1.0 mL; PBS), and fixed in ethanol (80%) for 30 minutes on ice. Fixed cells were spun at 500 g for 5 minutes, rehydrated with PBS (1 mL), and spun again to remove any traces of ethanol. Cells were stained with propidium iodide (250 µL; PI), which was prepared by adding PI (100 µL, 2 mg/ml, Sigma) and RNase A (3.5 µL of 30 mg/ml, Sigma) into PBS (10 mL). Cells were then analyzed at the Wistar Institute Flow Cytometry Core Facility using standard equipment, reagents, and methodologies known in the art.

The morphology of the cells was also noted. In agreement with our biochemical results and the MTS cell viability assay, compounds 3, 4, and staurosporine most drastically affected SiHa cells whereas the inactive analog had no effect (Table 3). DNA content analysis by flow cytometry indicated that the thiadiazolin-3,5-dione compounds caused an increase of apoptotic SiHa cells as did the non-specific kinase inhibitor staurosporine (Table 3). As noted, the percentage of cells in G0/G1 phase also decreased for these three compounds and the percentages of apoptotic cells do not correspond well with the percent of viable cells as determined by the MTS assay, which may be due to the fact that most apoptotic cells float and are lost during collection for FACS analysis. Another indicator of apoptosis was the fact that the morphology of SiHa cells treated with the thiadiazolidinediones resembled that of those treated with staurosporine: they became rounder in shape and were predominantly floating in solution. Cells treated with DMSO and the inactive analog maintained the elongated shape inherent in SiHa cells. These results are consistent with the MTS data and in vitro data, together supporting the interpretation that the thiadiazolin-3,5-dione compounds antagonize the proliferation ability of HPV-E7.

TABLE 3

Comparison of Compounds 3 and 4, an inactive analog, and staurosporine on the cell cycle and apoptosis in SiHa cells

| SiHa | % G0/G1 | % G2/M | % S | % Apoptotic |
| --- | --- | --- | --- | --- |
| DMSO | 72.9 | 15.9 | 10.7 | 1.1 |
| Compound 3 | 57.7 | 21.1 | 15.4 | 6.5 |
| Compound 4 | 49.2 | 20.0 | 15.8 | 15.2 |
| Staurosporine | 31.3 | 21.2 | 13.8 | 34.3 |
| Inactive analog | 71.8 | 16.3 | 11.3 | 0.9 |

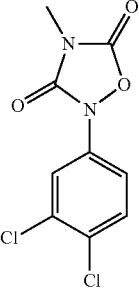

Example 11

Treatment of HPV in Mouse Model

Mice are generated as a model for human tumors associated with an HPV infection, as described in Li, PNAS USA, 99(25):16232-16236 (Dec. 10, 2002). Prior to administration of test compound or control, each mouse has a palpable skin tumor that serves as a surrogate for a human tumor expressing HPV-16 E7 protein, such as a human cervical carcinoma. Each mouse is independently administered, s.c. or i.v., an effective amount of one of compounds 1-7 and a control.

Daily physical examinations of each mouse are conducted, each examination monitoring the presence and physical characteristics of the skin tumor. Additionally, blood samples are withdrawn from the mice daily over a period of 6 months and tested for viral loads of HPV, using the methods provided in the prior examples.

It is anticipated that compounds 1-7 reduce viral loads of HPV shortly after administration. It is also expected that no HPV remains in blood samples from the mice withdrawn at 6 months. It is further anticipated that compounds 1-7 result in the reduction in tumor size, eventually leading to total tumor loss.

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "a compound" is understood to represent one or more compounds. As such, the terms "a" (or "an"), "one or more", and "at least one" are used interchangeably herein. As used herein, the term "about" means a variability of 10% from the reference given, unless otherwise specified. Technical and scientific terms used herein have the same meaning as commonly understood by one of ordinary skill in the art to which this invention belongs and by reference to published texts, which provide one skilled in the art with a general guide to many of the twins used in the present application.

What is claimed is:

1. A method for preventing disruption of pRb/E2F complexes, said method comprising administering a thiadiazolin-3,5-dione compound to a patient in need thereof, wherein said compound is:

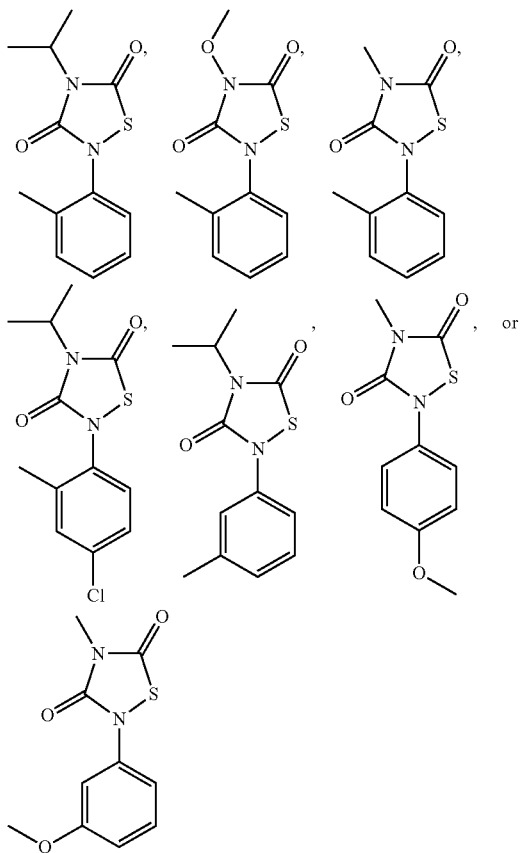

or a pharmaceutically acceptable salt thereof.

2. The method according to claim 1, further comprising administering a chemotherapeutic.

3. The method according to claim 1, further comprising treating said patient with radiation.

4. The method according to claim 1, wherein said administering treats a neoplastic disease.

5. The method according to claim 4, wherein the thiadiazolin-3,5-dione compound is

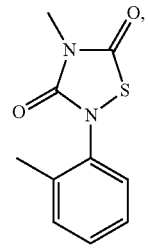

and wherein the neoplastic disease is cervical cancer.

6. The method according to claim 4, wherein said patient is infected with HPV or said neoplastic disease is caused by HPV infection.

7. The method according to claim 1, wherein said administering prevents HPV-E7 mediated E2F displacement from pRb or disrupts pRb/HPV-E7 complexes.

8. The method according to claim 1, wherein said administering prevents or treats genital warts or neoplastic disease caused by human papilloma virus.

9. The method according to claim 1, wherein said administering prevents interaction between pRb and a viral oncoprotein.

10. The method according to claim 1, wherein said administering prevents or treats a disease caused by a virus carrying a viral oncoprotein containing a L×C×E motif.

11. The method according to claim 10, wherein said viral oncoprotein is E7 from HPV.

12. The method according to claim 1, wherein the pharmaceutically acceptable salt is derived from pharmaceutically or physiologically acceptable acids, bases, alkali metals and alkaline earth metals.

13. The method according to claim 1, wherein said compound is administered with one or more suitable excipients or carriers.

* * * * *